US012291558B2

(12) United States Patent
Metelitsa et al.

(10) Patent No.: US 12,291,558 B2
(45) Date of Patent: May 6, 2025

(54) CD1D-RESTRICTED NKT CELLS AS A PLATFORM FOR OFF-THE-SHELF CANCER IMMUNOTHERAPY

(71) Applicant: Baylor College of Medicine, Houston, TX (US)

(72) Inventors: Leonid S. Metelitsa, Sugar Land, TX (US); Jingling Jin, Houston, TX (US); Bin Liu, Richmond, TX (US)

(73) Assignee: Baylor College of Medicine, Houston, TX (US)

( * ) Notice: Subject to any disclaimer, the term of this patent is extended or adjusted under 35 U.S.C. 154(b) by 487 days.

(21) Appl. No.: 16/637,986

(22) PCT Filed: Aug. 10, 2018

(86) PCT No.: PCT/US2018/046306
§ 371 (c)(1),
(2) Date: Feb. 10, 2020

(87) PCT Pub. No.: WO2019/033023
PCT Pub. Date: Feb. 14, 2019

(65) Prior Publication Data
US 2020/0216810 A1 Jul. 9, 2020

(30) Foreign Application Priority Data
Aug. 11, 2017 (EP) ..................... 17185992

(51) Int. Cl.
| | | |
|---|---|---|
| C12N 15/11 | (2006.01) | |
| A61K 39/00 | (2006.01) | |
| C07K 14/705 | (2006.01) | |
| C07K 14/725 | (2006.01) | |
| C12N 5/0783 | (2010.01) | |
| C12N 15/86 | (2006.01) | |

(52) U.S. Cl.
CPC ...... *C07K 14/7051* (2013.01); *A61K 39/4613* (2023.05); *A61K 39/4631* (2023.05); *A61K 39/464411* (2023.05); *A61K 39/464412* (2023.05); *A61K 39/464471* (2023.05); *C07K 14/70521* (2013.01); *C07K 14/70596* (2013.01); *C12N 5/0646* (2013.01); *C12N 15/11* (2013.01); *C12N 15/86* (2013.01); *A61K 2239/26* (2023.05); *A61K 2239/31* (2023.05); *A61K 2239/38* (2023.05); *A61K 2239/48* (2023.05); *C12N 2310/531* (2013.01); *C12N 2510/00* (2013.01); *C12N 2740/10043* (2013.01)

(58) Field of Classification Search
CPC .................................................. C12N 5/0646
USPC ..................................................... 424/93.21
See application file for complete search history.

(56) References Cited

U.S. PATENT DOCUMENTS

| | | |
|---|---|---|
| 2007/0078085 A1 | 4/2007 | Chung et al. |
| 2009/0258027 A1 | 10/2009 | Newell et al. |
| 2016/0009813 A1 | 1/2016 | Themeli et al. |
| 2016/0310532 A1 | 10/2016 | Metilitsa et al. |

FOREIGN PATENT DOCUMENTS

| | | |
|---|---|---|
| WO | WO 2005/108572 A1 | 11/2005 |
| WO | WO 2006/000830 A2 | 1/2006 |
| WO | WO 2008/103392 A2 | 8/2008 |
| WO | WO 2016/170320 A1 | 4/2016 |
| WO | WO 2016/069282 A1 | 5/2016 |
| WO | WO 2016/094679 A | 6/2016 |
| WO | WO 2017/001572 A1 | 1/2017 |
| WO | WO 2017/079673 A1 | 5/2017 |

OTHER PUBLICATIONS

O'Schaughnessy et al (The Oncologist, 2005, (Suppl 3): 20-29).*
Liu et al (Blood, 2015, 126(23): 3091).*
Bagnara et al (Haematologica, 2009, 94(7): 967-974).*
Pleyer et al (Nature Reviews Clinical Oncology, 2009, 6: 405-418).*
Gredell et al., "Impact of target mRNA structure on siRNA silencing efficiency: a large-scale study," *Biotechnology and Bioengineering*, 100(4): 744-755 (2008).
Maeda et al., "CD1d-Independent NKT Cells in $\beta_2$-Microglobulin-Deficient Mice Have Hybrid Phenotype and Function of NK and T Cells," *J. Immunology*, 172(10): 6115-6122 (May 15, 2004).
Moreno et al., "IFN-γ-Producing Human Invariant NKT Cells Promote Tumor-Associated Antigen-Specific Cytotoxic T Cell Responses," *J. Immunology*, 181(4): 2446-2454 (Jun. 29, 2008).
Van Luijn et al., "Absence of Class II-Associated Invariant Chain Peptide on Leukemic Blasts of Patients Promotes Activation of Autologous Leukemia-Reactive CD4$^+$ T Cells," *Cancer Research*, 71(7): 2507-2517 (Feb. 10, 2011).
U.S. Patent and Trademark Office, International Search Report in International Patent Application No. PCT/US2018/046306, 6 pp. (Nov. 29, 2018).
U.S. Patent and Trademark Office, Written Opinion in International Patent Application No. PCT/US2018/046306, 10 pp. (Nov. 29, 2018).
European Patent Office, Extended European Search Report in European Patent Application No. 17185992, 2 pp. (Oct. 19, 2017).
Atkins et al., "High-dose recombinant interleukin 2 therapy for patients with metastatic melanoma: analysis of 270 patients treated between 1985 and 1993," *J Clin Oncol* 17(7):2105-2116 (1999).
Bendelac et al., "CD1 recognition by mouse NK1+ T lymphocytes," *Science* 268(5212):863-865 (1995).

(Continued)

*Primary Examiner* — Sean E Aeder
(74) *Attorney, Agent, or Firm* — Norton Rose Fulbright US LLP

(57) ABSTRACT

An isolated human NKT cell or a plurality of cells thereof, having reduced or no detectable expression of endogenous beta-2-microglobulin (B2M); endogenous MHC class II-associated invariant chain (Ii); or both. Methods to generate the cell or cells, and methods of treatment using the cell or cells are also provided.

20 Claims, 20 Drawing Sheets
Specification includes a Sequence Listing.

(56) References Cited

OTHER PUBLICATIONS

Brentjens et al., "CD19-targeted T cells rapidly induce molecular remissions in adults with chemotherapy-refractory acute lymphoblastic leukemia," *Sci.Transl.Med.* 5(177):177ra138 (2013).
Dhodapkar et al., "A Reversible Defect in Natural Killer T Cell Function Characterizes the Progression of Premalignant to Malignant Multiple Myeloma," *J.Exp.Med.* (2003).
Dudley et al., "Cancer regression and autoimmunity in patients after clonal repopulation with antitumor lymphocytes," *Science* 298(5594):850-854 (2002).
Extended European Search Report in European Patent Application No. 18843435.1 dated Jun. 23, 2021.
Grupp et al., "Chimeric antigen receptor-modified T cells for acute lymphoid leukemia," *N.Engl.J.Med.* 368(16):1509-1518 (2013).
Gundry et al., "Highly Efficient Genome Editing of Murine and Human Hematopoietic Progenitor Cells by CRISPR/Cas9," *Cell Rep* 17(5):1453-1461.
Heczey et al., "Invariant NKT cells with chimeric antigen receptor provide a novel platform for safe and effective cancer immunotherapy," *Blood* 2014;124(18):2824-2833 (2014).
Kim et al., "The transcriptional programs of iNKT cells," *Semin. Immunol.* 27(1):26-32 (2015).
Kochenderfer et al., "B-cell depletion and remissions of malignancy along with cytokine-associated toxicity in a clinical trial of anti-CD19 chimeric-antigen-receptor-transduced T cells," *Blood* 119(12):2709-2720 (2012).
Koh et al., "Activation of Nonclassical CD1d-Restricted NK T Cells Induces Airway Hyperreactivity in β2-Microglubulin-Deficient Mice," *The Journal of Immunology* 181(7):4560-4569 (2008).
Krangel et al., "Assembly and maturation of HLA-A and HLA-B antigens in vivo," *Cell* 18(4):979-991 (1979).
Lanier, "NK cell recognition," *Annu Rev Immunol* 23:225-274 (2005).
Lantz, "An invariant T cell receptor alpha chain is used by a unique subset of major histocompatibility complex class I-specific CD4+ and CD4-8-T cells in mice and humans," *J.Exp.Med.* 180(3):1097-1106 (1994).
Metelitsa, "Anti-tumor potential of type-I NKT cells against CD1d-positive and CD1d-negative tumors in humans," *Clin.Immunol.* 140(2):119-129 (2011).
Morris et al., "NKT cell-dependent leukemia eradication following stem cell mobilization with potent G-CSF analogs," *J.Clin.Invest* 115(11):3093-3103.

Pillai et al., "Host NKT cells can prevent graft-versus-host disease and permit graft antitumor activity after bone marrow transplantation," *J.Immunol.* 178(10):6242-6251 (2007).
Porcelli et al., "Analysis of T cell antigen receptor (TCR) expression by human peripheral blood CD4-8-alpha/beta T cells demonstrates preferential use of several V beta genes and an invariant TCR alpha chain," *J.Exp.Med.* 178(1):1-16 (1993).
Porter et al., "Chimeric antigen receptor-modified T cells in chronic lymphoid leukemia," *N.Engl.J.Med.* 365(8):725-733 (2011).
Qasim et al., "Molecular remission of infant B-ALL after infusion of universal TALEN gene-edited CAR T cells," *Sci Transl Med* 9(374) (2017).
Ramos et al., "CAR-T Cell Therapy for Lymphoma," *Annu.Rev.Med.* (2015).
Singh et al., "Early memory phenotypes drive T cell proliferation in patients with pediatric malignancies," *Sci Transl Med* 8(320):320ra323 (2016).
Tahir et al., "Loss of IFN-gamma production by invariant NK T cells in advanced cancer," *J. Immunol.* 167(7):4046-4050 (2001).
Tian et al., "CD62L+ NKT cells have prolonged persistence and antitumor activity in vivo," *J Clin Invest* 126(6):2341-2355 (2016).
Turtle et al., "Clinical trials of CD19-targeted CAR-modified T cell therapy; a complex and varied landscape," *Expert Rev Hematol* 9(8):719-721 (2016).
Wong et al., "Genomic mapping of the MHC transctivator CIITA using an integrated ChIP-seq and genetical genomics approach," *Genome Biology* 5(494):1-15 (2014).
Yanagisawa et al., "Hyporesponsiveness to natural killer T-cell ligand alpha-galactosylceramide in cancer-bearing state mediated by CD11b+ Gr-1+ cells producing nitric oxide," *Cancer Res.* 66(23):11441-11446 (2006).
Balato et al., "Natural Killer T cells: An Unconventional T-cell Subset with Diverse Effector and Regulatory Functions." *Journal of Investigative Dermatology*, 129(7), pp. 1628-1642 (Mar. 2009) (electronic publication).
Cohen et al., "Shared and distinct transcriptional programs underlie the hybrid nature of iNKT cells," *Nat. Immuniol.* 14(1), pp. 90-99 (Jan. 2013) (electronic publication).
Ren et al. "Multiplex Genome Editing to Generate Universal CAR T Cells Resistant to PD1 Inhibition" Clin Cancer Res 2017;23:2255-2266. Published OnlineFirst Nov. 4, 2016, AACR American Association for Cancer Research.
Hurton et al. "Tethered IL-15 augments antitumor activity and promotes a stem-cell memory subset in tumor-specific T cells" PNAS, Published online Nov. 14, 2016, pp. E7788-E7797.
Gonzalez et al. "Amplification of RNAi—Targeting HLA mRNAs" Molecular Therapy vol. 11, No. 5, May 2005, pp. 811-818, The American Society of Gene Therapy.

\* cited by examiner

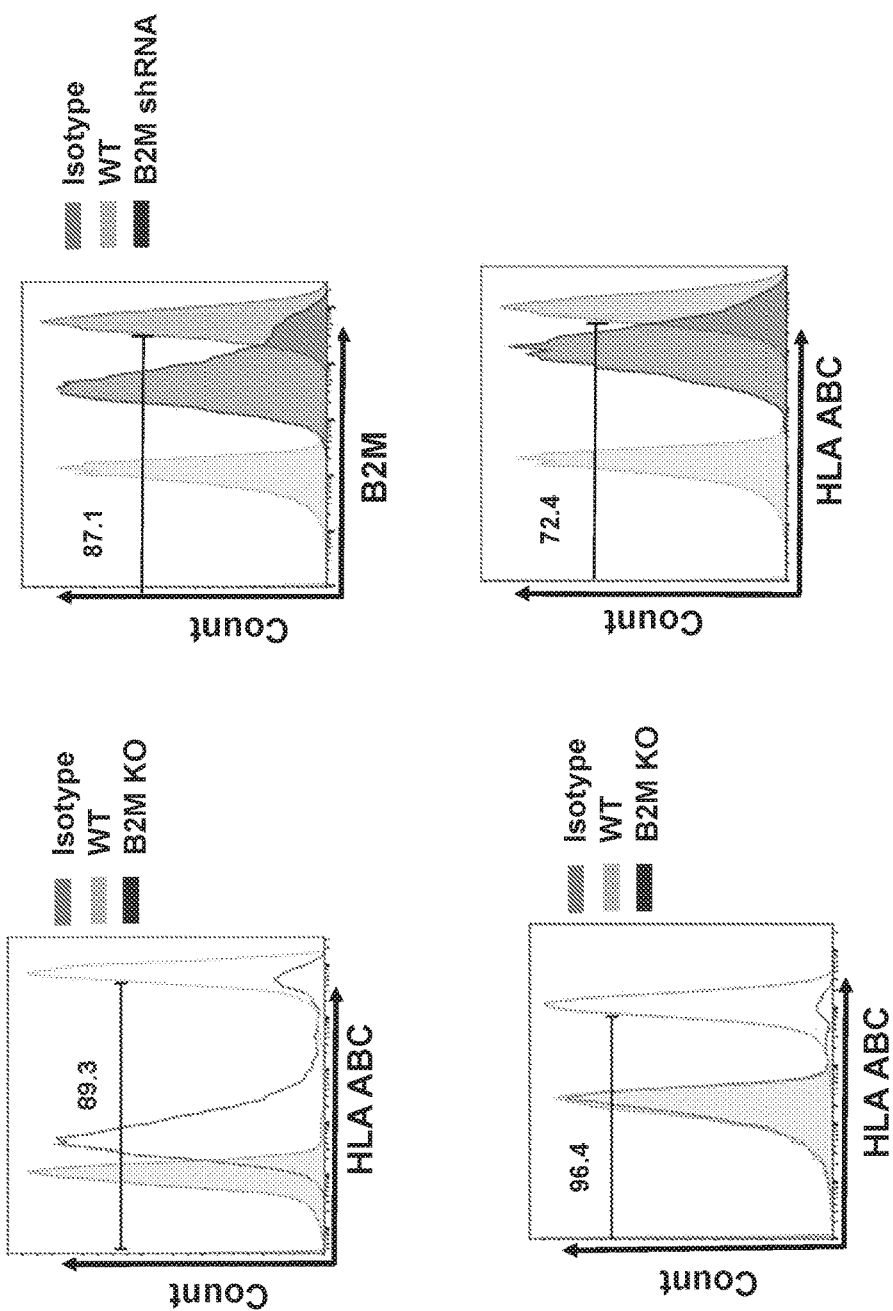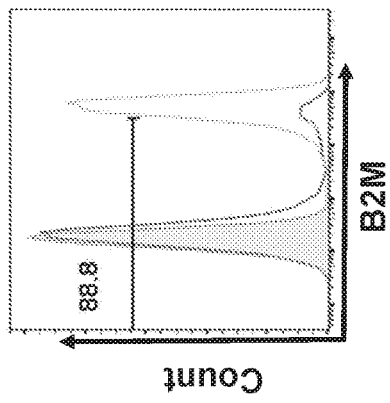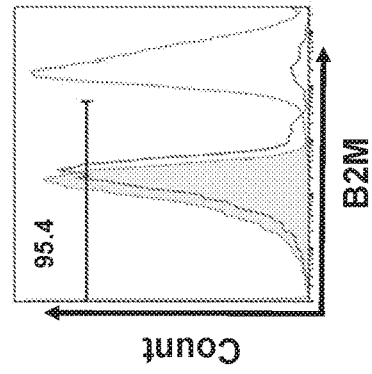

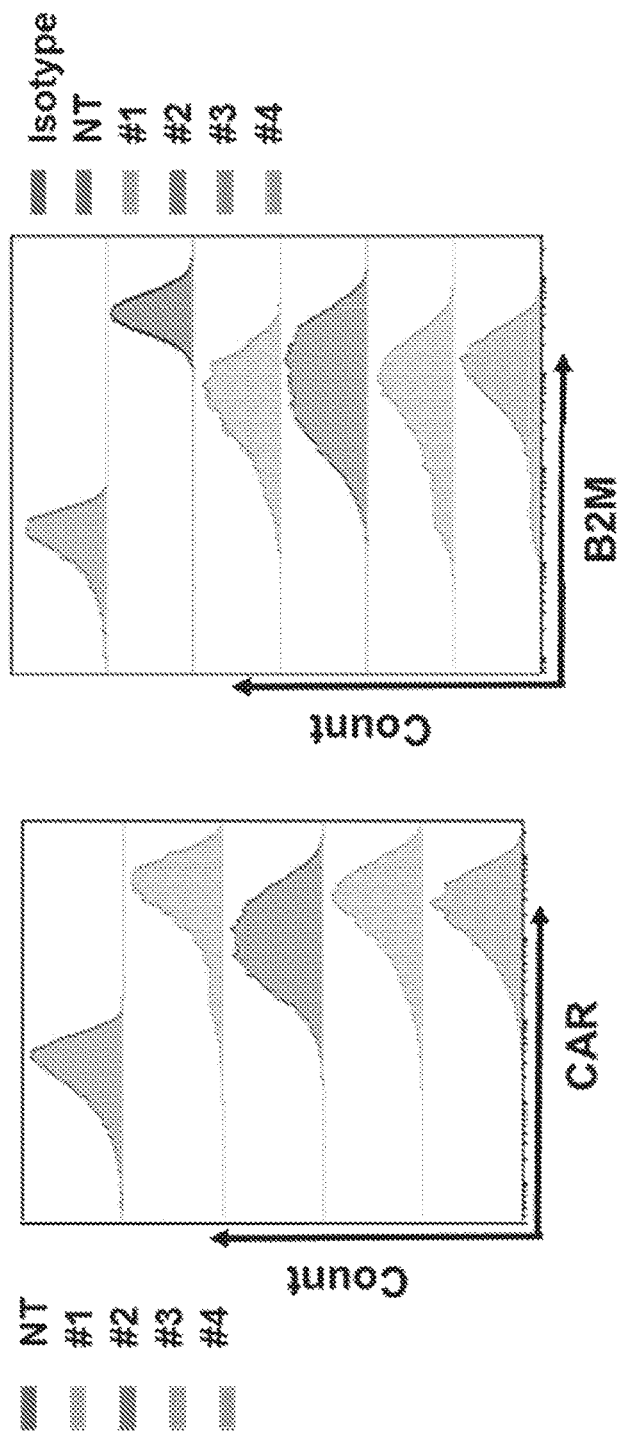

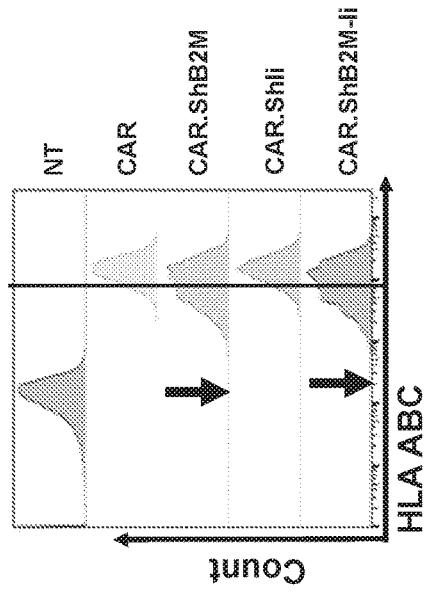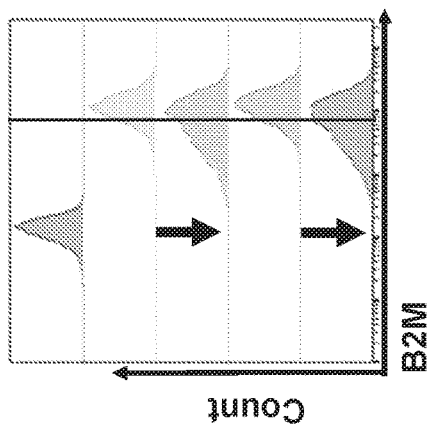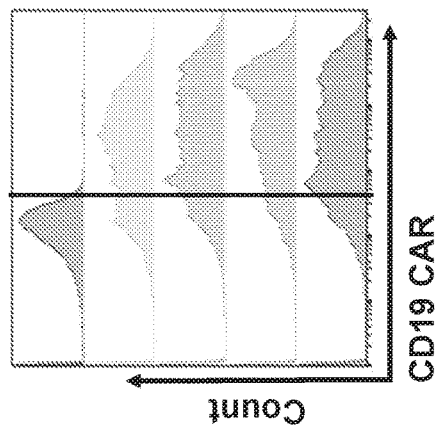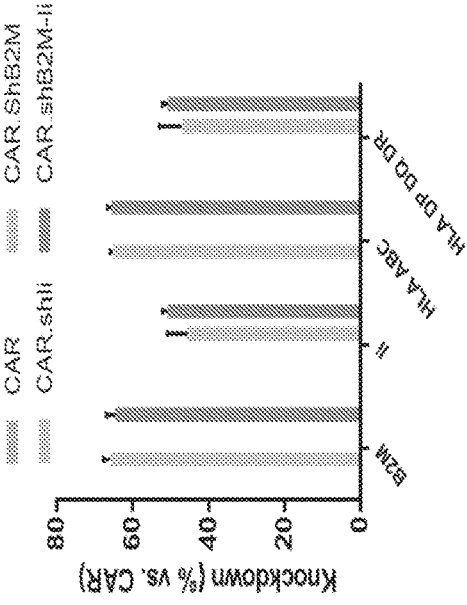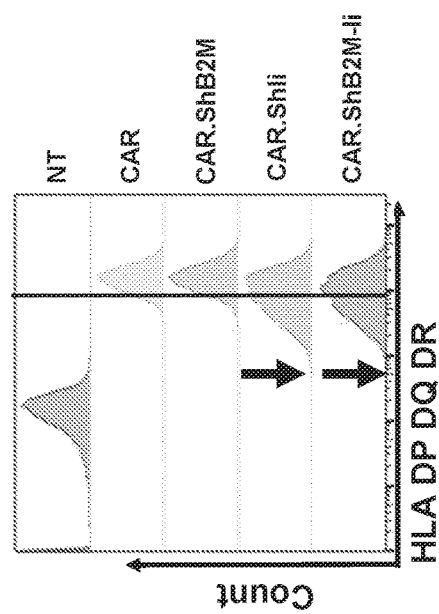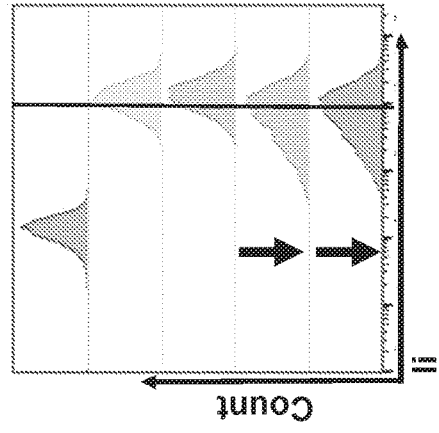

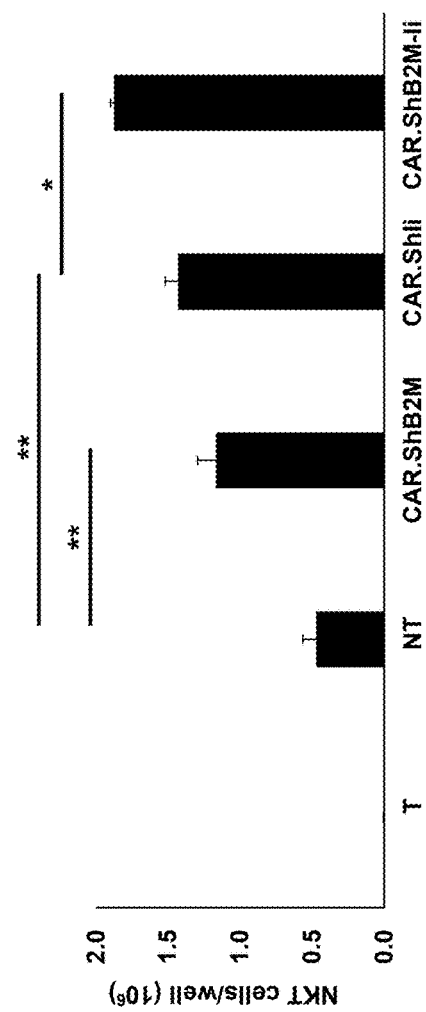
FIG. 14B
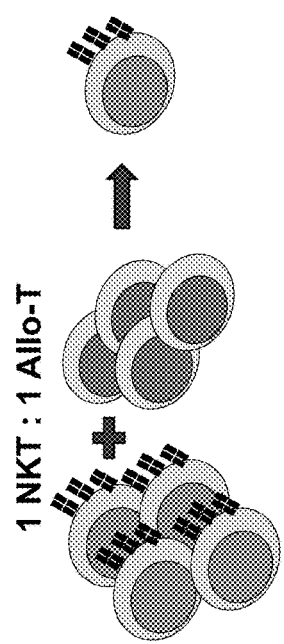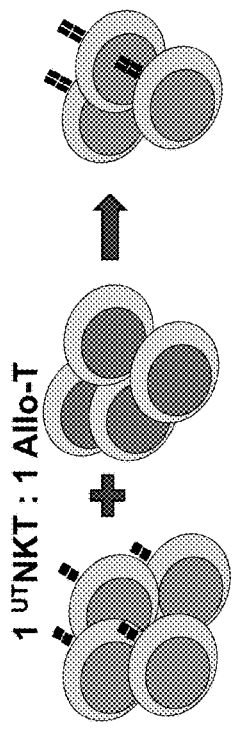
FIG. 14A

CD1D-RESTRICTED NKT CELLS AS A PLATFORM FOR OFF-THE-SHELF CANCER IMMUNOTHERAPY

CROSS-REFERENCE TO RELATED APPLICATIONS

This application is the U.S. national phase of International Patent Application PCT/US2018/046306, filed Aug. 10, 2018, which claims priority to European Patent Application Serial No. 17185992.9, filed Aug. 11, 2017, both of which are hereby incorporated by reference in their entireties herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3,438 Byte ASCII (Text) file named "747494_ST25" created on Feb. 10, 2020.

TECHNICAL FIELD

The present disclosure concerns at least the fields of cell biology, molecular biology, immunology, and medicine.

BACKGROUND

Cancer Immunotherapy with Autologous Tumor-Specific T Cells.

The strategy of isolating and expanding tumor-specific T cells followed by infusion (adoptive transfer) back to patients is a promising modality of cancer treatment. Such treatment has been successful in some patients with melanoma, who can have complete and sustained tumor regression following infusion of autologous melanoma-specific T cells (1). As a treatment for other less immunogenic malignancies, however, T-cell therapy has been limited by the paucity of molecularly-defined tumor antigens capable of eliciting a robust T-cell response, and by the difficulty of isolating these T cells from a tumor-bearing host.

Cancer Immunotherapy with CAR-Redirected Autologous T Cells.

The genetic modification of T cells with a chimeric antigen receptor (CAR) for re-directed antigen specificity is one strategy to generate effector cells for adoptive therapy that does not rely on pre-existing anti-tumor T-cell immunity. Recent clinical trials demonstrate that T cells redirected to the CD19 antigen can induce sustained complete responses in patients with B-cell leukemia and lymphoma (2-7). However, T cells obtained from lymphoma patients have a reduced proliferative capacity because of the effects of disease and chemotherapy. The reduction in T-cell expansion during product manufacture means that only 25% of newly diagnosed and as few as 12.5% of treated pediatric lymphoma patients could be infused with autologous CD19 CAR T cells (8). Similarly to lymphoma patients, defects in T cell numbers and functions are common in patients with many types of cancer (9-12). One way to overcome this limitation is to use T cells obtained from healthy individuals that are modified with a tumor-specific CAR and ex vivo expanded for infusion to cancer patients. However, beyond a small fraction of patients eligible for allogeneic stem cell transplantation, HLA-mismatched T cells cannot be used because they would cause graft-vs-host disease (GvHD) and/or be rejected by patient's immune system.

Genetic Deletion of TCR in T Cells to Avoid GvHD.

One approach to generate GvHD-incapable CAR T cells from an unmatched healthy donor was demonstrated by Qasim et al. using gene editing to simultaneously introduce a CAR and disrupt TCR in T cells (13). TCR gene was deleted from T cell genome in that study using transcription activator-like effector nuclease (TALEN) technology, which introduced off-target genetic alterations (13).

Natural Killer T Cells (NKTs) have Anti-Tumor Effector Functions and Naturally Avoid GvHD.

NKTs are an evolutionarily conserved subset of innate lymphocytes that are characterized by the expression of invariant TCR α-chain Vα24-Jα18 and by reactivity to glycolipids presented by the monomorphic HLA class-I-like molecule CD1d (14-17). NKTs have numerous anti-tumor properties and their numbers have been reported to correlate with good outcome in several types of cancer (18). Heczey A. et al and Gian T. et al. demonstrated that NKTs can be isolated from peripheral blood, transduced with a CAR and expanded to clinical scale for adoptive cell therapy applications (19, 20). Several studies have shown that donor-derived NKTs do not mediate GvHD and even may suppress it (21, 22). Therefore, allogeneic healthy donor-derived CAR NKTs could be used to treat cancer patients without a risk of GvHD that, in contrast to T cells, does not require additional genetic manipulation.

Elimination of Allogeneic Therapeutic Cells by Host Immune System.

All normal nucleated cells express HLA class I and therefore adoptively transferred therapeutic cells from HLA mismatched donors will be eliminated by the host immune system. T and NKT cells can also transiently express HLA class II when activated, and HLA class II mismatch triggers donor cell elimination by host CD4 T cells. A common approach to delay such rejection is to use of immunosuppressive host conditioning to allow a therapeutic window for effector cells to mediate anti-tumor activity before recovery of the host immune system. However, such approach is toxic to patients and may not allow complete tumor control due to insufficient persistence of the therapeutic effector cells.

Expression of HLA Class I Molecules on Cell Surface Depends on β2-Microglobulin (B2M).

It is well established that in order to be expressed on the cell surface HLA class I molecules require B2M (23). Hence targeting B2M in donor-derived effector cells would disrupt HLA class I expression and prevent their recognition by host CD8 T cells. However, HLA class I molecules also serve as inhibitory ligands for NK cells and the loss of B2M expression is expected to make donor cells susceptible to killing by host NK cells (24). It is unknown whether a certain level of B2M/HLA class I expression can be achieved in donor cells that would be sufficient to prevent activation of host CD8 T cells without triggering host NK-cell cytotoxicity. Finding such range of B2M expression in NKTs would enable a prolonged tolerance of cancer patients to therapeutic NKTs or CAR NKTs from HLA unmatched healthy donors that will allow lasting anti-tumor activity without a risk of GvHD.

Expression of HLA class II molecules on cell surface depends on HLA-DR antigens-associated invariant chain (Ii, also referred to as CD74). The invariant chain facilitates MHC class II's export from the ER and is required for proper antigen loading and surface expression of MHC class II/antigen complexes. T cells are known to transiently express MHC class II on their cell surface upon activation, e.g. antigen recognition. The disclosure describes the finding that NKT cells also upregulate MHC class II expression on the cell surface following TCR stimulation (FIG. 3A). Therefore, the inventors sought to attenuate NKT cell rejection by host CD4 T cells via downregulation of MHC class II by targeting Ii expression. Moreover, it was characterized whether combined targeting of B2M and Ii in NKTs would further prolong tolerance of cancer patients to therapeutic NKTs or CAR NKTs from HLA unmatched healthy donors and maximize their anti-tumor activity without a risk of GvHD.

BRIEF SUMMARY

Embodiments of the disclosure include cells, such as from a donor, that are manipulated to be tolerated by a host, for example to avoid undesirable host immune responses; methods of use of the cells are also encompassed in the disclosure, including as an immunotherapy. In specific embodiments, the cells are for use in immunotherapy and may be considered to be utilized off-the-shelf. The cells are suitable for adoptive therapy, in particular embodiments. The cells avoid GvHD in a subject, in particular embodiments. The cells may be utilized in one or more hosts, including cells from the same plurality of engineered cells for use in one or more hosts. In particular cases, the cells to be provided to a subject have had one manipulation to achieve the ability to avoid host immune cells and, in some cases, also to provide tumor specificity for cell destruction. In some cases the disclosure encompasses one-hit generation of tumor-specific and universally tolerated NKT cells from healthy donors for off-the-shelf immunotherapy, including for cancer. In particular cases, cells encompassed by the disclosure are able to prevent activation of allogeneic CD8 T cells or CD4 T cells including without triggering killing by allogeneic NK cells. In such cases the cells are NKT cells that are engineered to express little or no HLA class I molecules, and these cells, surprisingly, remain resistant to killing by the host NK cells. The NKT cells as used herein may include iNKT, UTNKT, or natural killer T cells, for example. In some cases donor cells are able to be utilized for immunotherapy of HLA unmatched subject, including those with cancer. In specific cases, RNA interference is used with B2M-specific shRNAs, and a range of B2M and HLA class I expression can be found in NKT cells that would prevent activation of allogeneic CD8 T cells without triggering killing by allogeneic NK cells. In specific cases, RNA interference is used with Ii-specific shRNAs, and downregulation of Ii and HLA class II expression can be found in NKT cells that would prevent activation of allogeneic CD4 T cells. In some specific cases, B2M-specific shRNA, Ii-specific shRNA, or both and a tumor-specific CAR can be engineered to be expressed within a single retroviral construct for a one-hit generation of tumor-specific and universally tolerated healthy donor-derived NKT cells for immunotherapy of HLA unmatched cancer patients. In particular embodiments, the cells are not derived from induced pluripotent stem cells. The cells are resistant to elimination by NK cells, in specific aspects.

In one embodiment of the disclosure, there is an isolated NKT cell or a plurality of cells thereof, having reduced expression of endogenous beta-2-microglobulin (B2M) and/or MHC class II-associated invariant chain (Ii), or both. The cells have reduced expression of B2M and/or Ii because of manipulation by the hand of man and are not located in nature or similar to cells in nature. The reduced expression may be further defined as a knockout or a knockdown in the cells. In specific embodiments, the cell or cells comprise one or more agents that target the B2M gene and/or Ii gene, such as one or more synthetic DNA or RNA that targets the B2M gene or Ii gene, for example the 3' end of the B2M or Ii gene. In certain cases, the synthetic RNA is a shRNA or a CRISPR guide RNA.

In particular embodiments of the disclosure, a cell or cells that have reduced expression of endogenous B2M and/or Ii comprise one or more engineered receptors, such as a chimeric antigen receptor or a T cell receptor. In some cases, the NKT cell or cells recombinantly express one or more cytokines and/or one or more cytokine receptors, such as IL-15, IL-15Ra, IL-7, IL-12, IL-18, IL-21, IL-27, IL-33, or a combination thereof. In some cases, the NKT cell or cells have reduced expression of a second endogenous gene. In particular cases the cell or cells are autologous or allogeneic in reference to a subject.

In one embodiment, there is a method of generating the NKT cell or cells as encompassed herein by exposing NKT cells to one or more agents that reduce expression of endogenous B2M and/or MHC class II-associated invariant chain (Ii) in the cell or cells. The agent may be of any kind, including without being limited to a DNA vector, morpholinos, an antisense RNA, antigomer RNA, siRNA, S-DNA, TALEN, Zinc finger nuclease (ZFN) or a CRISPR guide RNA. Said DNA vector encodes an agent that inactivates or reduces expression of one or more target gene. In some cases, the NKT cells are manipulated to express one or more entities other than manipulation to have reduced expression of endogenous B2M, such as manipulated to have one or more engineered receptors and/or one or more cytokines. In some cases cells other than NKT cells are employed.

In some embodiments, there are a cell or cells as encompassed herein for use in the treatment of a medical condition in a subject, such as cancer. In some cases, the cancer is of the brain, lung, breast, prostate, pancreas, skin, kidney, liver, testes, ovary, gall bladder, spleen, endometrium, cervix, esophagus, thyroid, pituitary gland, stomach, colon, anus, blood, bone, bladder, bile duct, head and neck, oral cavity, salivary gland, small intestine, and/or urethra, or premalignant conditions, such as myelodysplastic syndrome (MDS).

In specific embodiments there is a composition comprising an allogeneic cell or allogeneic cells as encompassed herein for use in the treatment of a medical condition, preferably cancer or a premalignant condition, in a subject.

In some embodiments, there is a method of treating a medical condition in a subject by providing to the subject an effective amount of one or more cells as encompassed herein. The medical condition may or may not be cancer. In some cases the cells are allogeneic in reference to the subject, although in alternative cases they are autologous to the subject. In particular embodiments they are NKT cells.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 2A, 2B, and 2C. CRISPR/Cas9 knockout and shRNA knockdown of β2-microglobulin (B2M) expression. (2A) Representative flow cytometry analysis of B2M expression (left) and HLA ABC expression (right) in NKT cells 96 h following electroporation with Cas9 only (green) or Cas9/hB2M-sgRNA (red). (2B) A representative flow cytometry analysis of B2M and HLA ABC expression in NKT cells after further purification by depletion of B2M positive cells using Anti-APC MicroBeads (Miltenyi Biotec) following electroporation with Cas9 only (green) or Cas9/hB2M-sgRNA (red) (2C) A representative flow cytometry analysis of Lentivirus-mediated B2M shRNA causing downregulation of B2M (top) and HLA ABC (bottom) expression in NKT cells. Results are from a representative of 5 donors tested.

FIGS. 6A and 6B. Generation of retroviral vectors that express CAR and shRNA. (6A) Schematic Diagram of CAR/shRNA constructs: U6 promoter and shRNA are put downstream of CAR with the opposite (1) or the same direction (2). Additionally, U6 promoter and shRNA are put upstream of EF1 promoter-driven CAR with the same (3) or the opposite direction (4). (6B) Flow cytometry analysis of CAR and B2M expression in NKT cells. Results are from a representative of 5 donors tested.

FIGS. 11A-11F. shRNA knockdown of B2M and Ii expression. (11A) Representative flow cytometry analysis of CD19 CAR expression. NKTs were transduced with the indicated constructs four days after antigenic stimulation and stained with Alexa 647-conjugated anti-FMC63 mAb. Non-transduced (NT) NKTs served as control. Representative flow cytometry analyses of (11B) B2M, (11C) HLA ABC, (11D) Ii, and (11E) HLA DP-DQ-DR expression in NKT cells transduced with indicated constructs or NT NKTs. Cells were stained with anti-FMC63 mAb and 1) PE-conjugated anti-B2M antibody with FITC-conjugated anti-HLA ABC antibody or 2) PE-conjugated anti-Ii antibody with FITC-conjugated anti-HLA DP-DQ-DR antibody. Samples were gated on CAR positive cells. Results are from a representative of 3-5 donors tested. (11F) Quantification of indicated gene knockdown in CAR-shRNA NKTs versus CAR NKTs.

FIGS. 14A and 14B. UTNKT cells are less susceptible to allogeneic T cell cytotoxicity than parental NKTs. (14A) Schematic of expected results for NKT and $^{UT}$NKT cells in T cell cytotoxicity assay. Allogeneic T cells will recognize MHC molecules on parental NKTs as foreign, leading to death of these NKT cells. Downregulation of MHC molecules on $^{UT}$NKTs will allow these cells to evade T cell cytotoxicity better than parental NKTs. (14B) Allogeneic T cells were incubated with CAR $^{UT}$NKTs or non-transduced (NT) NKTs at a 1:1 ratio for four days. NKT cell counts were determined by flow cytometry using counting beads (Invitrogen). * p<0.05, ** p<0.01 compared with NT NKTs.

DETAILED DESCRIPTION

Figure 1:
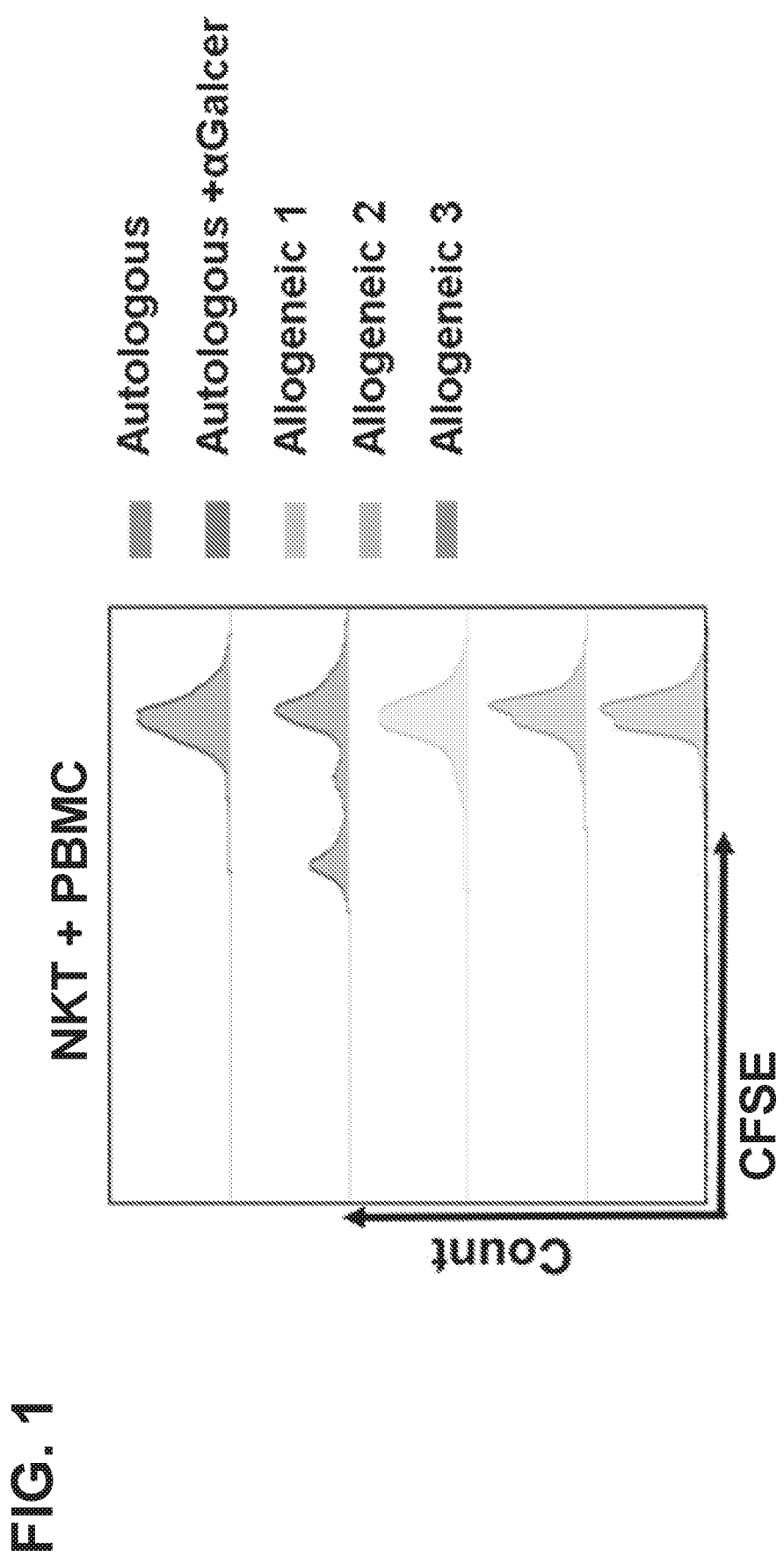
FIG. 1. NKT cells do not proliferate in the presence of allogeneic PBMC. Carboxyfluorescein succinimidyl ester (CFSE)-labeled NKT cells were co-cultured at 5:1 ratio with irradiated allogenic PBMC as stimulator cells. Autologous PBMC alone or pulsed with αGalCer served as a negative or a positive control, respectively. NKT cell proliferation was assessed by CFSE dilution as measured by flow cytometry on day 6. Results are from a representative of 4 experiments.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

The term "therapeutically effective amount" or "effective amount" as used herein refers to that amount which, when administered to a subject or patient for treating a disease, is sufficient to effect such treatment for the disease, including to ameliorate at least one symptom of the disease.

NKT cells having reduced expression of endogenous beta-2-microglobulin (B2M) and/or endogenous MHC class II-associated invariant chain (Ii) refers to cells wherein the level of endogenous beta-2-microglobulin (B2M) and/or endogenous MHC class II-associated invariant chain (Ii) expression is reduced when compared to unmodified NKT cells. In one embodiment, the level of endogenous beta-2-microglobulin (B2M) and/or endogenous MHC class II-associated invariant chain (Ii) expression is reduced by at least 50%, 55%, 60%, 65%, 70%, 75%, 80%, 85%, 90%, 95%, more preferably 100%.

The terms "downregulating", "downregulation" and the like refers to the decrease, reduction, elimination and/or inhibition of gene expression of one or more genes. As such, the term encompasses both terms "knockdown" and "knockout".

As used herein, the term "knockdown" refers to the decrease or elimination of gene expression of one or more genes.

The term "knockout" as used herein refers to the ablation of gene expression of one or more genes.

As used herein, the term "endogenous" refers to any material from or produced inside a cell, whereas the term "exogenous" refers to any material introduced from or produced outside an cell.

As used herein, the term "recombinantly engineered receptor" refers to a cell surface receptor that is generated by the hand of man using standard techniques for genetic recombination.

I. Modified NKTs According to the Disclosure are Resistant to Allo-NK Cell Cytotoxicity The present disclosure demonstrates that NKT cells can be isolated and ex vivo-expanded from healthy donors to large numbers while preserving the phenotype of highly functional cells, providing a basis for producing NKT cell-based allogeneic therapeutic products for therapeutic applications, such as adoptive cancer immunotherapy.

Owing to the NKT TCR restriction by the monomorphic CD1d, which is identical in all humans, the disclosure experimentally demonstrates that NKT cells do not react to PBMC from unrelated donors. These results indicate that unlike conventional T cells, allogeneic NKTs would not mediate GvHD when transferred to unrelated recipients.

Like any other cells, NKTs express HLA class I molecules and are subject to elimination by the immune system of HLA mismatched recipients, primarily by HLA class I-restricted CD8 T cells. The existing knowledge in the field teaches that HLA class I expression can be eliminated or reduced by targeting B2M expression. However, it is also known that HLA class I molecules serve as inhibitory ligands for NK cells so that targeting B2M expression is expected to trigger NK-cell mediated killing. Thus, the existing state of the art in the field suggest that B2M elimination or downregulation in NKTs or any other type of effector lymphocytes used in cancer immunotherapy would subject the cells to allo-NK cell cytotoxicity. In this disclosure it is demonstrated for the first time that either complete elimination of B2M expression, such as via CRISPR-mediated gene deletion, or a graded downregulation of B2M expression, such as via shRNA-mediated RNA interference, are equally effective in reducing NKT-cell stimulation by allogeneic CD8 and CD4 T cells.

Unexpectedly, as shown herein the majority of NKTs remained resistant to allo-NK cell cytotoxicity after CRISPR-mediated B2M knockout and even more so after shRNA-mediated B2M knockdown. Considering that shRNA-mediated B2M gene knockdown in NKTs is equally effective in reducing T-cell alloreactivity, but makes NKTs less susceptible to allo-NK cell cytotoxicity compared with CRISPR-mediated B2M gene knockout, in some embodiments shRNA is utilized for targeting B2M expression in NKTs and likely other effector lymphocytes (e.g. T, NK, γ/δ T, MAIT, ILCs, etc.) for adoptive cell therapy applications in allogeneic settings. Moreover, in contrast to CRISPR and similar genome-editing methods (e.g., TALEN, ZFN), shRNA does not cause permanent genetic changes in target cells, providing a clinically safer option in at least some cases.

Finally, it is demonstrated herein for the first time that a B2M-specific shRNA and a tumor-specific CAR can be engineered to be expressed within a single retroviral construct for a one-hit generation of tumor-specific and universally tolerated healthy donor-derived NKT cells for immunotherapy of HLA unmatched cancer patients.

II. Cells of the Disclosure

In particular embodiments, cells of the disclosure are cells that have anti-tumor effector functions and/or that are able to avoid graft-versus-host disease. Although in particular embodiments the cells are NKT cells, in other embodiments the cells are T, NK, γ/δ T, MAIT, or ILCs. The cells are not derived from induced pluripotent stem cells, in at least some cases. In specific embodiments, the cells have reduced or no expression of HLA class I and/or class II molecules and/or of one or more HLA class II molecules. In specific embodiments, the cells are unable to be recognized by certain host T cells, such as host CD8 T cells and/or host CD4 T cells. In particular embodiments, the cells are manipulated to reduce or eliminate expression of B2M, for example so that expression of HLA class I molecules is reduced or eliminated in the cells. Additionally or alternatively, the cells are manipulated to reduce or eliminate expression of Ii, for example so that expression of HLA class II molecules is reduced or eliminated in the cells. In particular embodiments, the cells of the disclosure are designed such that the host NK cells are unable to kill the cells encompassed by the disclosure. In some embodiments, the cells of the disclosure are not allo-reactive with host stimulator cells, such as host PBMCs and lack the ability to mediate GvHD when adoptively transferred to allogeneic host. In specific embodiments, the cells are resistant to elimination by NK cells.

In certain embodiments, the present disclosure concerns cells that have reduced expression of B2M. The cells that have reduced expression of B2M may have B2M expression that is undetectable by standard means in the art or that is detectable but reduced in the level of expression compared to cells that have not been manipulated by the hand of man to have reduced endogenous expression. The cells may be defined as having a B2M knockout or knockdown in expression. In doing so, the cells are HLA class I-negative, in specific embodiments. In some embodiments, the present disclosure concerns cells that have reduced expression of Ii. The cells that have reduced expression of Ii may have Ii expression that is undetectable by standard means in the art or that is detectable but reduced in the level of expression compared to cells that have not been manipulated by the hand of man to have reduced endogenous expression. The cells may be defined as having a Ii knockout or knockdown in expression. In doing so, the cells are HLA class II-negative, in specific embodiments.

In alternative cases, instead of a partial or complete reduction in the level of expression of B2M or Ii, the cell may be engineered to express a respective non-functional version. For example, the cell may be manipulated to express a B2M and/or Ii that is a non-functional fragment of its full-length or that is full-length but that has one or more mutations (point mutation, inversion, deletion, etc.) that impart an impairment of its standard functionality. An example of a B2M mutant is one with a defective MHC1 alpha 1 alpha 2 domain interaction (Hill et al., 2003).

In particular embodiments, there is one or more isolated human NKT cells, including a plurality of cells thereof, that have reduced or no detectable expression of the following: (a) endogenous beta-2-microglobulin (B2M); (b) endogenous MHC class II-associated invariant chain (Ii); or (c) both, wherein the cells are not derived from induced pluripotent stem cells, and wherein the cells are suitable for adoptive therapy. In particular embodiments, such characteristics are the direct or indirect reason for the cells to be resistant to elimination by NK cells.

In some cases, the cells are isolated from donors, including healthy donors, wherein the cells are selected for one or more certain traits. For example, the cells may be selected for the expression of one or more certain markers, such as surface markers. In specific embodiments, such marker(s) may be associated with specific beneficial functions, such as an increased ability for the cells to expand, persist in vivo after adoptive transfer, and/or to resist exhaustion after repeated rounds of tumor cell killing compared to cells that lack the marker(s), for example. In specific embodiments, the cells are selected to express a biomarker selected from the group consisting of CD62L, CD4, and a combination thereof, and/or to lack expression or have low expression of PD1, LAG3, TIM3, TIGIT, etc.

In specific embodiments, in addition to the cells having reduced expression of B2M and/or Ii, the cells may be engineered to express one or more other non-natural entities, such as one or more receptors. The receptor(s) may be of any type, and one cell may have more than one receptor in addition to having reduced expression of B2M and/or Ii. In particular cases the receptor(s) are recombinantly engineered receptors. For example, the receptor may be a chimeric antigen receptor (CAR), a chimeric cytokine receptor, T cell receptors, and so forth. In cases wherein the cell is modified to express one or more CARs, a single CAR(s) may target one or more antigens, including one or more tumor antigens. The tumor antigen targeted by a receptor may include 5T4, 8H9, $\alpha_v\beta_6$ integrin, BCMA, B7-H3, B7-H6, CAIX, CA9, CD19, CD20, CD22, CD30, CD33, CD38, CD44, CD44v6, CD44v7/8, CD70, CD123, CD138, CD171, CEA, CSPG4, EGFR, EGFR family including ErbB2 (HER2), EGFRvIII, EGP2, EGP40, ERBB3, ERBB4, ErbB3/4, EPCAM, EphA2, EpCAM, FAP, FBP, fetal AchR, FRα, GD2, GD3, Glypican-3 (GPC3), HLA-A1+MAGE1, HLA-A1+NY-ESO-1, IL-11Rα, IL-13Rα2, Lambda, Lewis-Y, Kappa, KDR, MCSP, Mesothelin, Muc1, Muc16, NCAM, NKG2D Ligands, NY-ESO-1, PRAME, PSC1, PSCA, PSMA, ROR1, SP17, Survivin, TAG72, TEMs, carcinoembryonic antigen, HMW-MAA, or VEGFR2, for example. A CAR may be first generation (comprises CD3 zeta chain), second generation (comprises CD3 zeta chain and one intracellular signaling co-stimulatory endodomain), third generation (comprises CD3 zeta chain and two or more intracellular signaling co stimulatory endodomains), fourth generation (inducibly release recombinant immune modifiers), and so forth. In specific embodiments, the CAR comprises co-stimulatory endodomains selected from the group consisting of CD28, OX40, 4-1BB, ICOS, CD40, CD30, CD27, or a combination thereof. Additionally or alternatively, the cells may express one or more recombinant T cell receptors (TCR). In some embodiments, such TCR may be modified to achieve high levels of cell surface. suppression as e.g. described in WO2016170320A1. In some embodiments, such TCR comprises a recombinant interchain disulfide bond between extracellular constant domain residues as e.g. described in WO2006000830A2. In specific embodiments, recombinant TCR expressing cells may further be engineered to inducibly release recombinant immune modifiers. Exemplary recombinant immune modifiers are antibodies, fragments thereof (such as e.g., scFvs), or antibody derivatives, which may e.g. target TNF alpha and/or PD-L1.

In some embodiments, the cells are manipulated to express recombinantly one or more gene products that would be beneficial to the anti-tumor activity, expansion, and/or growth of the cells. Such gene products include one or more cytokines (including at least, IL-15, IL-7, IL-12, IL-18, IL-21, IL-27, IL-33, antibody fragments or derivatives such as scFvs or bispecifics (e.g., targeting cancer antigens and/or checkpoint inhibitors), or a combination thereof), and/or pro-survival cytokine receptors for example IL-7Ra or IL-15Ra. The NKT cells selected to express certain one or more gene products may or may not be modified to express the gene product(s) recombinantly also. In some embodiments, the cells are manipulated to downregulate expression of one or more gene products that target an inhibitory receptor in the cell (e.g., PD1, LAG3, TIM3, TIGIT, TGFbR1, IL-10R, etc.).

In cases wherein the cells are manipulated to express an entity in addition to being manipulated to have reduced expression of B2M and/or Ii, the entity may or may not be introduced into the cell by a vector. In some cases, the agent for reducing expression of B2M and/or Ii and the entity other than the agent (such as an engineered receptor) are introduced into the cell on the same vector, although in other cases they are on different vectors. In some cases, the cell may be manipulated to have reduced expression of B2M and/or Ii prior to manipulation of the cell to express an additional entity, although in some cases the cell is manipulated to have reduced expression of B2M and/or Ii subsequent to manipulation of the cell to express an additional entity. In cases wherein they are on the same vector, the agent for reducing expression of B2M and/or Ii and the additional entity may be on the same expression construct and regulated by the same or different gene regulatory sequence(s) or a different expression construct having different gene regulatory sequence(s). In cases where a single vector is used, the agent for reducing expression of B2M may be 5' or 3' in a 5' to 3' direction in relation to the additional entity, or vice versa.

In cases wherein the cells are lymphocyte subsets that are not NKT cells, one can assess whether the level of B2M downregulation by shRNA is sufficient for reducing allogenecity without triggering allo-NK cell killing that could be used for cancer immunotherapy: T cells (which may also have deletion of TCR), γ/δ T cells, MAIT cells, NK cells, and ILCs are examples. In cases wherein non-NKT cells are utilized, the non-NKT cells may be required to undergo manipulation not required by the NKT cells.

In some embodiments, in the cells the MHC class II-associated invariant chain (Ii) is targeted with an agent (such as shRNA or other standard methods) for downregulation, thereby affording downregulation of HLA class II expression in the cells and further reducing allo-reactivity mediated by CD4 T cells. In such cases the cells may also be manipulated to express recombinantly another entity such as an engineered receptor and/or one or more cytokines, and so forth. In specific embodiments the cell comprises a viral (for example, retroviral) construct that encodes a CAR with Ii shRNA, although in certain cases the CAR and the Ii shRNA are on separate constructs or vectors. In some cases the cells have downregulated Ii expression but are not manipulated to have downregulation of expression of B2M.

In some embodiments, a NKT cell line is provided which stably expresses reduced levels of B2M and/or Ii or wherein expression of B2M and/or Ii is stably inactivated.

In particular embodiments, the cells express constructs (for example, retroviral constructs) that have downregulation of both B2M and Ii. In such cells, there may be expression of a CAR and/or other gene product as well. In specific embodiments, the cells express a CAR and have downregulation of both B2M and Ii (for example, have both B2M and Ii shRNAs). In other specific embodiments, the cells express a recombinant TCR and have downregulation of both B2M and Ii (for example, have both B2M and Ii shRNAs).

In some embodiments, the cells express a complex CAR, e.g., a CAR construct and additionally one or more cytokines (e.g., IL-15, IL-7, IL-12, IL-18, IL-21, IL-27, IL-33, a combination thereof, etc.) and/or cytokine receptors (receptors for IL-15, IL-7, IL-12, IL-18, IL-21, IL-27, IL-33, a combination thereof). In preferred embodiments thereof, the cells additionally express and shRNA for B2M, Ii, or both (or one or more other agents that target B2M, Ii, or both other than shRNA).

In some embodiments, the cells express one or more recombinantly engineered receptors, a B2M and/or Ii shRNA, and a second shRNA targeting another gene. In specific embodiments, the cells express a CAR, a B2M and/or Ii shRNA, and another shRNA targets a gene encoding an inhibitory receptor in the cells (e.g., PD1, LAG3, TIM3, TIGIT, TGFbR1, IL-10R, etc.).

In specific embodiments, the cells comprise an inducible suicide gene (such as caspase-9 or thymidine kinase, for example).

In another aspect, vectors are provided for a one-hit generation of tumor-specific and allo-NK-cell resistant NKT cells for immunotherapy. A vector used to manipulate the cells of the disclosure may be of any kind, including a viral vector or a non-viral vector. Non-viral vectors include plasmids, and viral vectors include lentiviral, retroviral, adenoviral, adeno-associated viral vectors, herpes simplex virus, and so forth. Such vector encodes for one or more engineered receptor(s) as defined above together with an agent that reduces expression of B2M and/or Ii. Such agent may be selected from the group consisting of shRNA, CRISPR system, such as CRISPR guide RNA, morpholinos, siRNA, antisense RNA, antigomer RNA, S-DNA, ZFNs, and TALENs.

Particular embodiments include viral constructs (such as retroviral or lentiviral) that simultaneously encode a CAR and a shRNA in NKTs.

The allogenic cells that are modified to downregulate B2M and/or Ii may be obtained commercially. The allogenic cells may be obtained from a donor and immediately processed to have downregulation of B2M and/or Ii, or the allogenic cells may be obtained from a repository, including in a fresh or frozen state.

III. Methods of Producing the Cells

In particular embodiments, there are methods of generating cells encompassed by the disclosure, including cells that have downregulation of B2M, Ii, or both. Such cells also may express one or more types of engineered receptors.

In some cases the method of producing the cells includes the step of obtaining cells to be manipulated, although in other cases the obtaining step is not included in the method. The donor cells may be obtained from a healthy subject, including one that does not have cancer, for example. The cells may or may not be expanded prior to recombinant manipulation to downregulate B2M and/or Ii. In some methods, the cells may be selected to express or lack expression of a marker, for example whereupon such selection allows for enhanced expansion of the cells. For example, part of the method of producing the cells may include steps for selecting for expression of CD62L, expression of CD4, and/or reduced or absent expression of PD1.

Cells may be produced using any one or more agents to effect downregulation of expression of B2M, Ii, or both. Such agents may be of any kind, but in specific embodiments the agent is a shRNA, CRISPR system, such as CRISPR guide RNA, morpholinos, siRNA, antisense RNA, antigomer RNA, S-DNA, TALENs, ZFNs, and so forth. An example of a B2M polynucleotide sequence to design nucleic acids that target B2M is in GenBank® Accession No. NM_004048. An example of an Ii polynucleotide to design nucleic acids that target Ii (CD74) is in the GenBank® Accession No. NC_000005. Any shRNA used to generate cells of the disclosure may target any region of the target nucleic acid, including the 5' end or 3' end, or a region therein between, for example exon 1 or exon 2, etc.

In particular embodiments, cells of the disclosure are manipulated to express an entity other than the agent that downregulates B2M and/or Ii, and the entity may be an engineered receptor (in particular as defined above), a cytokine, or another gene product. In specific embodiments, the entity is a chimeric antigen receptor (CAR). In some cases, the step that renders the cell to downregulate B2M and/or Ii is a concomitant step that renders the cells capable of expressing the other entity, although in alternative cases these are different steps. In specific embodiments, when the cells are simultaneously engineered to downregulate B2M and/or Ii and to express a CAR (for example), it is because the agent that downregulates B2M and/or Ii and the CAR are expressed on the same vector. However, in other cases the agent that downregulates B2M and/or Ii and the CAR are expressed from different vectors.

Methods of the disclosure may or may not include steps of generating vectors to be introduced to the donor cells (or expanded progeny thereof). Production of recombinant vectors is well-known in the art, and a variety of vectors may be utilized, including viral or non-viral vectors. In cases where a single vector encompasses both an agent that downregulates B2M and/or Ii and an engineered receptor such as a CAR (for example), the skilled artisan recognizes that design of the vector will take size constraints (for example) for the cells into consideration.

In cases wherein the cells to be manipulated are T cells, the endogenous T cell receptor of the cells may be downregulated or knocked out, such as using routine methods in the art.

IV. Methods of Using the Cells

Embodiments of the disclosure include a cell or cells encompassed by the disclosure for use in the treatment of a medical condition, such as cancer or a premalignant condition, in a subject. The cells may be used for any type of cancer, including neuroblastoma, breast cancer, cervical cancer, ovary cancer, endometrial cancer, melanoma, bladder cancer, lung cancer, pancreatic cancer, colon cancer, prostate cancer, hematopoietic tumors of lymphoid lineage, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, tumors of mesenchymal origin, fibrosarcoma, rhabdomyosarcomas, melanoma, uveal melanoma, teratocarcinoma, neuroblastoma, glioma, glioblastoma, benign tumor of the skin, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer myelodysplastic syndrome, mesothelioma, angiosarcoma, Kaposi's sarcoma, carcinoid, oesophagastric, fallopian tube cancer, peritoneal cancer, papillary serous mullerian cancer, malignant ascites, gastrointestinal stromal tumor (GIST), or a hereditary cancer syndrome selected from Li-Fraumeni syndrome and Von Hippel-Lindau syndrome (VHL). In specific embodiments, the premalignant condition is myelodysplastic syndrome (MDS).

In particular embodiments of the disclosure there are methods of treating a disease with cells encompassed in the disclosure. Although the disease may be of any kind, in specific embodiments the disease is cancer. Any type of cancer may be treated, including neuroblastoma, breast cancer, cervical cancer, ovary cancer, endometrial cancer, melanoma, bladder cancer, lung cancer, pancreatic cancer, colon cancer, prostate cancer, hematopoietic tumors of lymphoid lineage, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), tumors of mesenchymal origin, fibrosarcoma, rhabdomyosarcomas, melanoma, uveal melanoma, teratocarcinoma, neuroblastoma, glioma, glioblastoma, benign tumor of the skin, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), or a hereditary cancer syndrome selected from Li-Fraumeni syndrome and Von Hippel-Lindau syndrome (VHL). In specific embodiments, the disease is myelodysplastic syndrome (MDS).

An effective amount of cells of the disclosure having reduced expression of B2M, Ii, or both, are provided to a subject in need of therapy with the cells. The amount may be of any quantity as long as at least one symptom of the disease is ameliorated. In specific embodiments, the cells are provided in a range of at least from about $1 \times 10^6$ to about $1 \times 10^9$ cells, even more desirably, from about $1 \times 10^7$ to about $1 \times 10^9$ cells, although any suitable amount can be utilized either above, e.g., greater than $1 \times 10^9$ cells, or below, e.g., less than $1 \times 10^7$ cells. In specific embodiments, one or more doses of the cells are provided to the subject, and subsequent doses may be separated on the order of minutes, hours, days, weeks, months or years. In some cases, separate deliveries of the cells have different amounts of cells. For example, an initial dose of the cells may be greater or lower than one or more subsequent doses.

The individual being treated may be an adult, adolescent, child, infant or animal. The individual may be a mammal, including a human, dog, cat, horse, cow, sheep, pig, and so forth. The individual may be of any gender, race, genetic background, and so forth. The individual may or may not have a personal and/or family history of cancer. The cells to be manipulated for downregulation of expression of B2M and/or Ii may or may not be obtained from a family member. In cases wherein the individual has cancer, the cancer may be of any stage or grade, and the cancer may be primary, metastatic, recurrent, sensitive, refractory, and so forth.

In some cases, one or more therapies in addition to the immunotherapy of the disclosure may be provided to the subject, such as surgery, radiation, hormone therapy, another, nonidentical immunotherapy, chemotherapy, or a combination thereof.

In some cases, the cells are employed for prevention of cancer in a subject, including, for example, a subject with a personal and/or family history of cancer.

Cells may be delivered to the subject in any suitable manner, including by injection, for example. It is in particular envisaged that the cells are administered to the subject via infusion or injection. Administration of the suitable compositions may be effected by different ways, e.g., by intravenous, subcutaneous, intraperitoneal, intramuscular, topical, parenteral, transdermal, intraluminal, intra-arterial, intrathecal or intradermal administration. The cells may be provided by direct injection into a cancer. Administration of the cells may be systemic or local.

The cells may or may not be targeted to a hypoxic environment associated with the cancer. In such cases, any regulatory element(s) to effect expression from an expression construct(s) in the cell may be effective in hypoxic environments.

In some embodiments, compositions comprising allogeneic NKTs as described herein for use in the treatment of a medical condition, such as cancer or a premalignant condition in an individual are provided. Such compositions are off-the shelf products which can be administered to any individual, regardless whether the HLA matches or not. Such composition has significant advantages for patients with regards to immediate availability, safety and therapeutic potential. Further to the cells described herein, said compositions may comprise, without being limited to, suspending agents, anti-oxidants, buffers, bacteriostats and solutes.

V. Kits

Any of the cell compositions described herein and/or reagents to produce and/or use the cell compositions may be comprised in a kit. In a non-limiting example, cells or reagents to manipulate cells may be comprised in a kit. In certain embodiments, cells that have reduced expression of B2M and/or Ii, or a population of cells that comprises NKT cells that have reduced expression of B2M and/or Ii, may be comprised in a kit. Such a kit may or may not have one or more reagents for manipulation of cells. Such reagents include small molecules, proteins, nucleic acids, antibodies, buffers, primers, nucleotides, salts, and/or a combination thereof, for example. Nucleic acids (DNA or RNA) or other agents that are capable of directly or indirectly reducing expression of B2M and/or Ii may be included in the kit, such as shRNA or CRISPR guide RNA. Nucleic acids that encode one or more cytokines, or cytokines themselves, may be included in the kit. Proteins, such as cytokines or antibodies, including agonistic monoclonal antibodies, may be included in the kit. Substrates that comprise the antibodies, or naked substrates themselves, may be included in the kit. Cells that comprise antigen presenting cell activity or reagents to generate same may be included in the kit. Nucleotides that encode engineered receptors, such as chimeric antigen receptors or chimeric cytokine receptors or engineered T-cell receptors, may be included in the kit, including one or more reagents to generate same.

In particular aspects, the kit comprises the cell therapy of the disclosure and also another therapy for a particular medical condition, such as a cancer therapy. In some cases, the kit, in addition to the cell therapy embodiments, also includes a second cancer therapy, such as chemotherapy, hormone therapy, and/or immunotherapy, for example. The kit(s) may be tailored to a particular cancer for a subject and comprise respective second cancer therapies for the subject.

The kits may comprise suitably aliquoted compositions of the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also may generally contain a second, third or other additional container into which the additional components may be separately placed. However, various combinations of components may be comprised in a vial. The kits of the present disclosure also will typically include a means for containing the composition and any other reagent containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Tumor-Specific and Universally Tolerated Nkt Cells from Healthy Donors for Off-the-Shelf Cancer Immunotherapy Screen of healthy donors to select candidates with highly functional NKTs.

Since NKT cell frequency in human PBMC varies from less than 0.01% to more than 1%, we first analyzed NKT cell frequency among PBMCs isolated from prospective healthy donors according to our IRB approved protocol. Next, we expanded NKTs for 12 days in culture using developed in our lab protocol and quantified the rate of their expansion and expression of key surface markers, associated with functional potential: CD62L, CD4 and PD1. We have characterized 12 healthy donors. At least 3 donors (#6, 7, 8) have very high NKT-cell expansion potential with good retention of CD62L and low PD1 expression (Table 1).

NKTs could proliferate only in response to their specific ligand, aGalCer, but not to autologous or allogeneic PBMC from 3 unmatched donors. These results indicate that NKT cells are not allo-reactive.

Targeting B2M expression in NKTs.

In order to achieve full B2M gene knockout in NKTs, we used CRISPR/Cas9 technology (25). Single guide (sg)RNA sequences for B2M were identified using the CRISPRscan algorithm (http://www.crisprscan.org). sgRNA (10 µg) was incubated with Cas9 protein, 10 µg (PNA Bio), for 10-15 min at room temperature and electroporated into $3 \times 10^6$ NKT cells. The optimized electroporation condition for NKT cells was 1600V, 10 ms and 3 pulses using a Neon transfection system (ThermoFisher Scientific). The sgRNA sequence for this experiment was GGCCACGGAGCGAGACATCT (SEQ ID NO:1). FIG. 2A shows that B2M expression was lost in 88% of NKT cells. To further enrich B2M-negative cells, we used negative selection by depleting B2M-positive cells by MACS sorting using APC-conjugated anti-B2M mAb and anti-APC MicroBeads. The obtained negative fraction contained >95% B2M- and HLA class I (ABC)-negative NKT cells (FIG. 2B).

Next, we tested five B2M-targeting short hairpin (sh) RNA constructs to achieve different levels of B2M gene downregulation (knockdown). B2M-specific shRNA expression was achieved using the lentiviral expression system from Sigma Mission® shRNA service (Sigma).

TABLE 1

NKT cell expansion from healthy donors.
NKT cells were isolated and expanded from prospective healthy donors. iNKT cell frequency and the rate of expansion were calculated at days 0 and 12, respectively.
The expression of CD62L, CD4 and PD1 was quantified using flow cytometry.

| Donor ID | PBMC (Million) | NKT day 0 (Million) | Percentage (%) | NKT DAY 12 (Million) | Expand (Fold) | CD62 High (%) | PD1 High (%) | CD62High/ PD1High ratio | CD4High (%) |
|---|---|---|---|---|---|---|---|---|---|
| 1  | 80  | 0.05 | 0.06 | 36  | 720  | 86.50 | 59.20 | 1.46 | 33.40 |
| 2  | 50  | 0.08 | 0.16 | 60  | 750  | 85.33 | 47.60 | 1.79 | 56.00 |
| 3  | 180 | 0.10 | 0.05 | 80  | 800  | 83.26 | 53.20 | 1.67 | 65.00 |
| 4  | 70  | 0.11 | 0.12 | 90  | 750  | 75.90 | 39.20 | 2.08 | 27.40 |
| 5  | 70  | 0 10 | 0.17 | 60  | 600  | 78.80 | 35.60 | 2.29 | 59.10 |
| 6  | 50  | 0.12 | 0.13 | 96  | 873  | 78.00 | 25.40 | 3.07 | 60.40 |
| 7  | 50  | 0.20 | 0.40 | 240 | 1200 | 67.15 | 29.75 | 2.25 | 48.75 |
| 8  | 80  | 0.30 | 0.49 | 288 | 960  | 85.55 | 28.65 | 2.90 | 42.56 |
| 9  | 70  | 0.15 | 0.22 | 132 | 600  | 71.85 | 25.10 | 2.87 | 86.05 |
| 10 | 50  | 0.09 | 0.18 | 10  | 111  | 29.85 | 18.35 | 1.62 | 56.30 |
| 11 | 60  | 0.19 | 0.33 | 63  | 331  | 51.00 | 40.00 | 1.28 | 53.70 |
| 12 | 80  | 0.30 | 0.38 | 60  | 200  | 40.20 | 27.00 | 1.48 | 26.10 |

Testing Allo-Reactivity NKT Cells.

Since NKTs are restricted by the monomorphic CD1d, they are not expected to react to allogeneic cells. To test this assumption, we performed one-way allo-MLR cultures using irradiated PBMC as stimulator cells and NKTs from unrelated donors as responder cells. Autologous PBMC served as a negative control and autologous PBMC pulsed with NKT-cell ligand aGalCer were used as a positive control. Proliferation of the responder cells was analyzed by assessing CFSE dilution. NKT cells were freshly isolated from buffy coat, washed twice, resuspended at $1 \times 10^7$ cells/ml in PBS, and incubated with 2.5 µM carboxyfluorescein succinimidyl ester (CFSE; CellTrace™ CFSE Cell Proliferation Kit, ThermoFisher Scientific) for 5 min. Labeled cells were spun, resuspended in culture media at $10^6$ cells/ml, and cultured in the presence of irradiated PBMC. Cell proliferation was examined on days 6 by measurement of CFSE dilution using flow cytometry. FIG. 1 shows that The following 5 shRNA sequences have been tested:

(SEQ ID NO: 2)
1. GTACCGGAGGTTTGAAGATGCCGCATTTCTCGAGAAATGCGGCAT
CTTCAAACCTTTTTTG;

(SEQ ID NO: 3)
2. CCGGCTGGTCTTTCTATCTCTTGTACTCGAGTACAAGAGATAGAA
AGACCAGTTTTG;

(SEQ ID NO: 4)
3. CCGGCAGCAGAGAATGGAAAGTCAACTCGAGTTGACTTTCCATTC
TCTGCTGTTTTG;

-continued (SEQ ID NO: 5)
4. CGGTCCGACATTGAAGTTGACTTACTCGAGTAAGTCAACTTCAAT
GTCGGATTTTTG; and (SEQ ID NO: 6)
5. CCGGCCCAAGATAGTTAAGTGGGATCTCGAGATCCCACTTAACTA
TCTTGGGTTTTTG.

Viral supernatant was made by co-transfecting HEK-293T cells with the packaging vectors. These shRNA viral particles were transduced into NKT cells with 8 μg/ml of hexadimethrine bromide (Polybrene, H9268, Sigma-Aldrich, St. Louis, MO, USA). B2M knockdown was confirmed by FACS. We were able to knockdown B2M to various degrees ranging from 60% to 90% with the most effective construct that was tested (SEQ ID NO:2) shown in FIG. 2C. This shRNA targets exon-2 in human B2M coding sequence.

Targeting Ii Expression in NKTs.

Figure 3B:
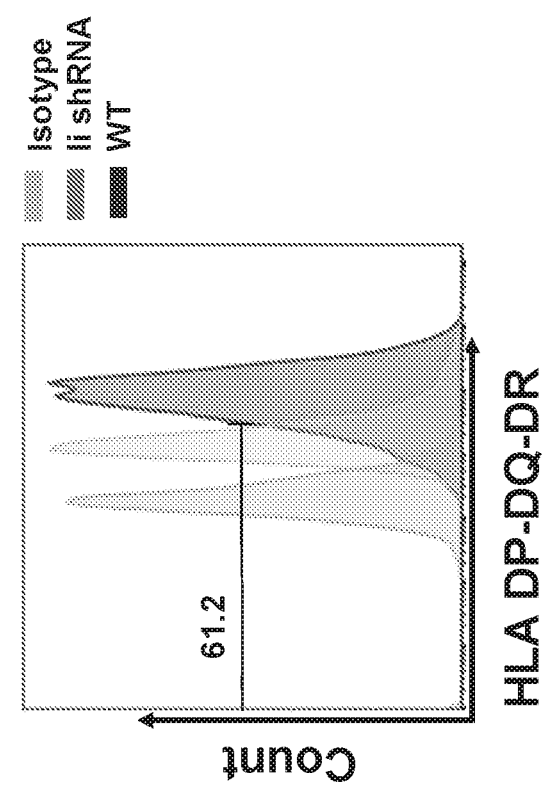
FIGS. 3A and 3B. Knockdown of HLA class II expression using Ii (CD74)-targeted shRNA. (3A) Representative flow cytometry analysis of HLA DP-DQ-DR expression in resting NKT cells (day 15 after stimulation) and activated NKT cells (day 2 after stimulation) using Pacific Blue-conjugated anti-HLA DP-DQ-DR mAb. (3B) Representative flow cytometry analysis of lentivirus-mediated Ii shRNA causing downregulation of HLA DP-DQ-DR on the surface of transduced NKT cells. Results are from a representative of 5 donors tested.
Figure 3A:
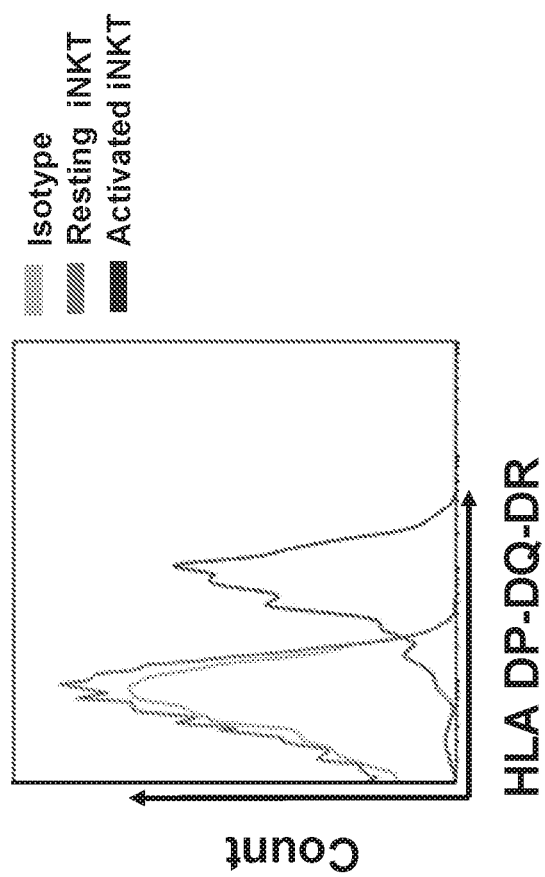

While it is known that T cell upregulate HLA class II expression upon activation, the status of HLA class II expression in human NKTs has not been examined to our knowledge. To answer this question, we performed flow cytometry analysis of HLA class II expression on resting NKT cells and then 2 days after their activation with α-galactosylceramide. FIG. 3A demonstrates that like T cells, NKTs do not express HLA class II in the absence of stimulation and readily upregulate surface expression of these molecules after antigenic stimulation. Next, we showed that HLA class II expression in activated NKTs can be effectively downregulated using an Ii-specific shRNA (FIG. 3B).

We tested five Ii-targeting short hairpin (sh)RNA constructs to achieve different levels of Ii gene downregulation (knockdown). Ii-specific shRNA expression was achieved using the lentiviral expression system from Sigma Mission® shRNA service (Sigma).

The following 5 Ii shRNA sequences have been tested, as examples:

(SEQ ID NO: 7)
1. CCGGGACCATAGACTGGAAGGTCTTCTCGAGAAGACCTTCCAGTC
TATGGTCTTTTT;

(SEQ ID NO: 8)
2. CCGGCCACCAAGTATGGCAACATGACTCGAGTCATGTTGCCATAC
TTGGTGGTTTTT;

(SEQ ID NO: 9)
3. CCGGCGCGACCTTATCTCCAACAATCTCGAGATTGTTGGAGATAA
GGTCGCGTTTTT;

(SEQ ID NO: 10)
4. CCGGCCACACAGCTACAGCTTTCTTCTCGAGAAGAAAGCTGTAGC
TGTGTGGTTTTT; and (SEQ ID NO: 11)
5. CCGGGAGAACCTGAGACACCTTAAGCTCGAGCTTAAGGTGTCTCA
GGTTCTCTTTTTG.

Viral supernatant was made by co-transfecting HEK-293T cells with the packaging vectors. These shRNA viral particles were transduced into NKT cells with 8 μg/ml of hexadimethrine bromide (Polybrene, H9268, Sigma-Aldrich, St. Louis, MO, USA). Ii knockdown was confirmed by FACS. We were able to knockdown Ii to various degrees ranging from 51.2% to 75.6% with the most effective construct that was tested (SEQ ID NO:7). This shRNA targets CDS in human Ii coding sequence.

Testing Allogenicity of $B2M^{null}$, $B2M^{low}$, and $Ii^{low}$ NKTs.

Figure 4A:
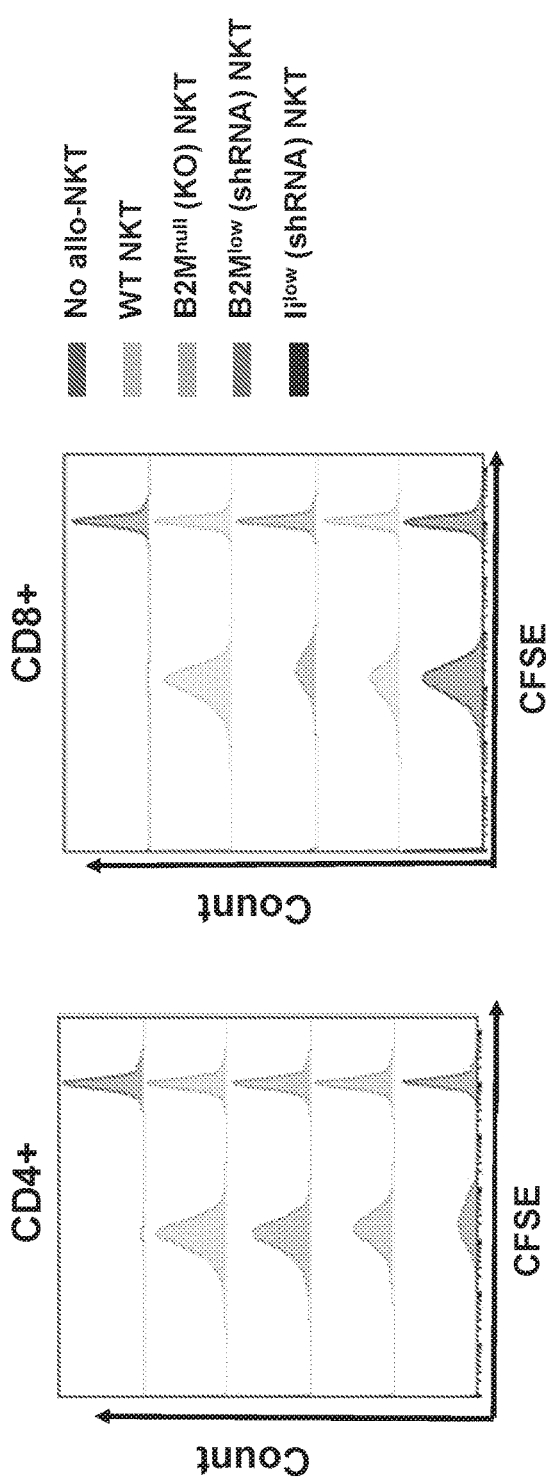
FIGS. 4A and 4B. B2M-targeting with CRISPR and shRNA are equally effective in reducing NKT-cell stimulation of CD4+ and CD8+ T cells in an allogeneic mixed lymphocyte reaction (MLR) assay. (4A) CFSE-labeled T cells were co-cultured at 5:1 ratio with WT, B2M$^{null}$ (CRISPR), B2M$^{low}$ (shRNA), or Ii$^{low}$ (shRNA) NKTs. Proliferation of CD8+ and CD4+ T cells was assessed on day 5 after stimulation as measured by CFSE dilution. (4B) Results are from a representative of 3 donors tested. *P<0.05, **p<0.01 compared with WT NKTs.
Figure 4B:
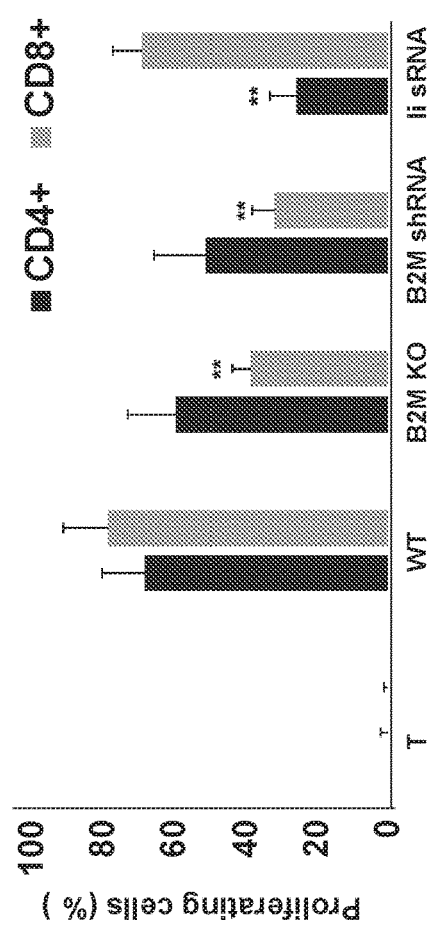

To determine the effect of CRISPR-mediated B2M knockout and shRNA-mediated B2M knockdown in NKTs on their ability to stimulate allo-reactive responses, we performed a one-way allo-MLR assay using irradiated NKTs as stimulator cells and magnetically sorted CD8 and CD4 T cells from unrelated donors as responder cells. T cells in the absence of allogeneic NKTs were used as a negative control. Allogeneic NKTs with wild type (WT) B2M were used as a positive control. In the experimental conditions, WT NKTs were replaced with CRISPR-induced $B2M^{null}$ or shRNA (SEQ ID NO:2)-induced $B2M^{low}$ NKTs as stimulator cells. We also generated $Ii^{low}$ NKTs using Ii-shRNA (SEQ ID NO:7). Proliferation of the responder cells was analyzed by assessing CFSE dilution by flow cytometry on day 5 of culture. We also stained cells for CD8 and CD4 markers to quantify proliferation of the respective T cell subsets. FIGS. 4A and 4B demonstrate that compared to WT B2M, $B2M^{null}$ NKTs reduced CD8 T cell proliferation from 74.1% to 38.5% (P<0.01). As expected, B2M and HLA class I expression did not significantly affect proliferation of CD4 T cells which are restricted by HLA class II molecules. Accordingly, $Ii^{low}$ NKTs reduced CD4 T cell proliferation from 68.1% to 31.6% (P<0.01), but did not affect proliferation of CD8 T cells.

Surprisingly, shRNA-mediated reduction of B2M/HLA-ABC expression in NKTs achieved equally effective suppression of allo-reactive CD8 T cell responses as the one that was achieved by CRISPR-mediated complete loss of B2M/HLA-ABC expression. These results demonstrate for the first time that there is a range of B2M/HLA-ABC expression in NKTs that can be tolerated by allogeneic T cells. This knowledge has immediate practical implications as it justifies the use of a safer shRNA technology instead of CRISPR or other genome-editing methods for a graded downregulation of B2M in NKTs and likely other effector cells from unrelated donors for adoptive cell therapy applications.

Testing susceptibility of $B2M^{null}$ and $B2M^{low}$ to Allo-NK Cells.

Figure 5A:
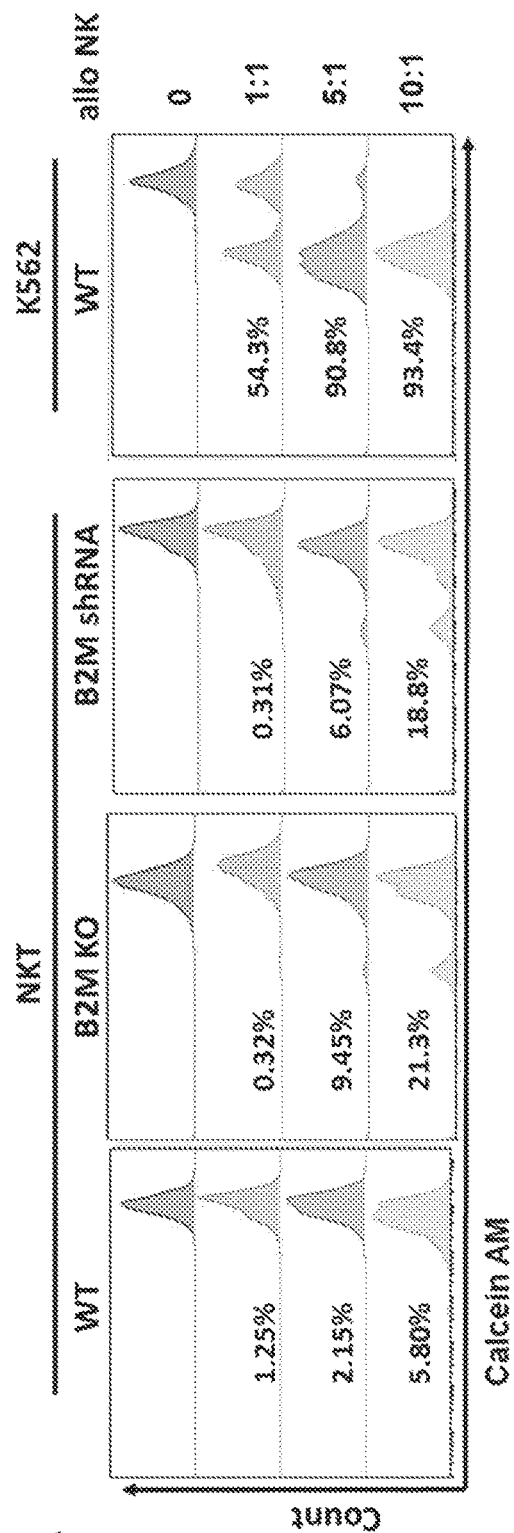
FIGS. 5A and 5B. B2M$^{null/low}$ NKTs are minimally susceptible to allo NK-cell cytotoxicity. (5A) The healthy donor-derived WT, B2M$^{null}$ (CRISPR) or B2M$^{low}$ (shRNA) NKT cells were labeled with calcein-AM and incubated 4 hours with allogeneic NK cells derived from an unrelated healthy donor at effector-to-target ratios of 10:1, 5:1, and 1:1. NK-sensitive K562 cells that naturally lack inhibitory HLA class I ligands were used as a positive control. (5B) Quantification of the mean percentage of specific lysis is shown. Data represent mean±SD. N=3; *P<0.05, **p<0.01 compared with the control WT cells.
Figure 5B:
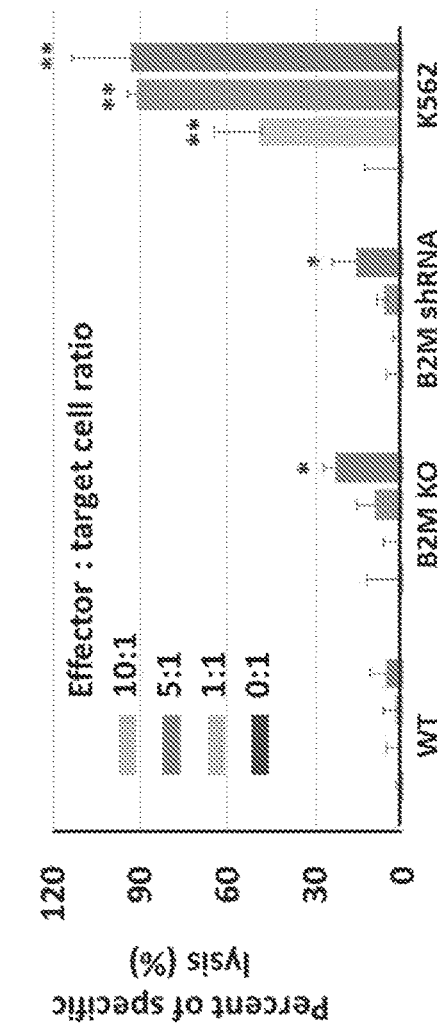

HLA class I molecules serve as major inhibitory ligands for NK cells and the loss of B2M expression is expected to make donor cells susceptible to killing by host NK cells (24). It is unknown, however, whether a certain level of B2M/HLA class I can be achieved in donor cells, in particular in NKT cells that would be sufficient to prevent activation of host CD8 T cells without triggering host NK-cell cytotoxicity. Therefore, we tested susceptibility of $B2M^{null}$ and $B2M^{low}$ NKTs to killing by allogeneic NK cells, using wildtype (WT) NKT cells as a negative control and NK-sensitive K562 cells that naturally lack inhibitory HLA class I ligands as a positive control. NKT or K562 cells as target cells were labeled with a viability dye calcein-AM followed by 4-hr co-culture with allogeneic NK cells as effector cells that were obtained by negative magnetic sorting from unrelated donors. Autologous NK cells were used as a negative control. The cytotoxic activity of NK cells was quantified by the loss of calcein-AM fluorescence in target cells as measured by flow cytometry. FIG. 5 demonstrates that unlike K562 cells, NKTs remained largely resistant to NK cell cytotoxicity even after complete loss of B2M expression. Indeed, only 21.3% of $B2M^{null}$ NKTs were killed by allo-NK cells at 10:1 effector to target ratio whereas nearly 100% of K562 cells were killed under the same conditions. B2M$^{low}$ NKTs were even more resistant than B2M$^{null}$ cells as only 18.8% of the former were killed by allo-NK cells at 10:1 effector to target ratio. Therefore, contrary to expectations, the results demonstrate for the first time that about 80% of NKTs remain resistant to allo-NK cell cytotoxicity even after complete genetic loss of B2M expression. Moreover, shRNA-mediated downregulation of B2M expression in NKTs makes them even more resistant to allo-NK-cell cytotoxicity compared to CRISPR-mediated B2M knockout.

Figure 6A:
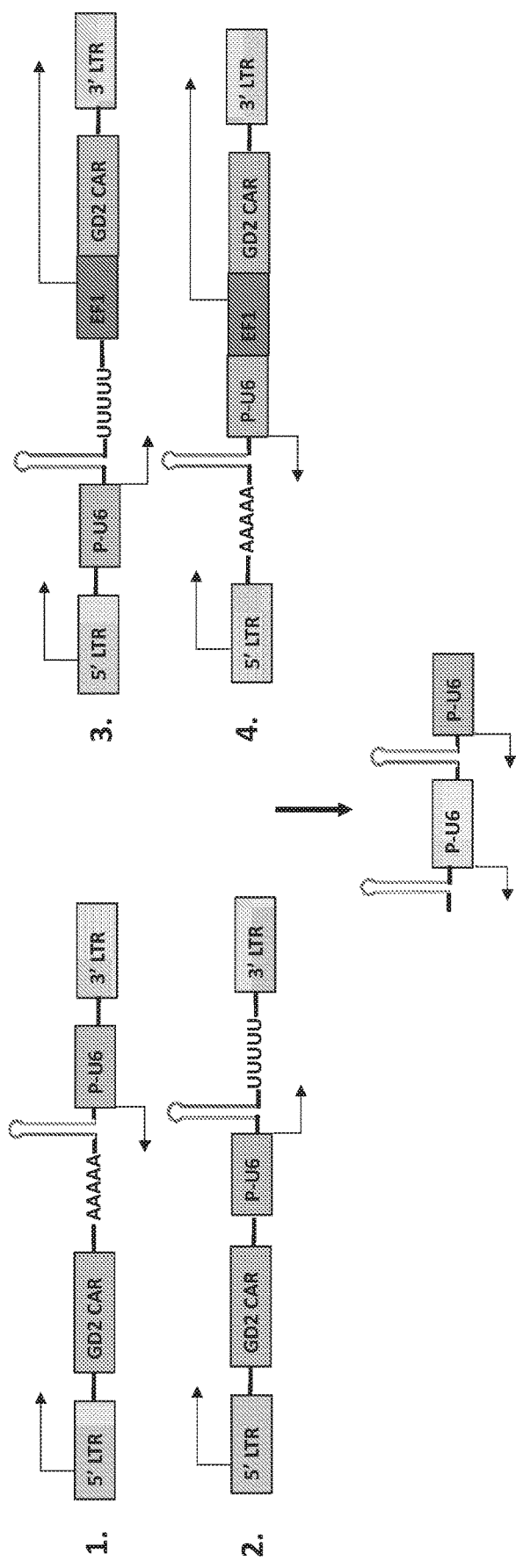

Design of Retroviral Vectors Encoding Both a CAR Construct and B2M shRNA and/or Ii shRNA To test whether a CAR and a shRNA can be effectively expressed within the same retroviral vectors, we have constructed retroviral vectors encoding a GD2-specific CAR and B2M shRNA (SEQ ID NO:2) and/or Ii shRNA (SEQ ID NO:7), as shown in FIG. 6A. In order to clone the shRNA(s) into a retroviral vector, we added one G before the sense shRNA sequence to serve as a transcription start site, and five T after the antisense shRNA sequence to serve a transcription stop site. The resultant shRNA sequence is the following:

```
                              (SEQ ID NO: 12)
CTGGTCTTTCTATCTCTTGTACTCGAGTACAAGAGATAGAAAGACCAG (SEQ ID NO: 13)
GACCATAGACTGGAAGGTCTTCTCGAGAAGACCTTCCAGTCTATGGTC
```

B2M shRNA was placed under control of U6 promoter and U6-shRNA was ligated into sphI site in forward or reverse direction while CAR expression was driven by an endogenous retroviral LTR or EF1 promoter (FIG. 6A). NKT cell transduction with CAR.GD2/B2M shRNA resulted in effective CAR expression. All 4 constructs achieved simultaneous expression of CAR and B2M downregulation in NKTs with construct #1 being the most effective (FIG. 6B).

Significance of Certain Embodiments of the Disclosure
1) NKT cells can be isolated and ex vivo-expanded from healthy donors to large numbers while preserving the phenotype of highly functional cells. These donor-derived NKTs can be used as a source of therapeutic products for adoptive cancer immunotherapy.
2) NKT cells do not proliferate in response to PBMC from unrelated donors, consistent with the inability of NKT TCR to recognize HLA molecules.
3) B2M-targeting with CRISPR and shRNA are equally effective in reducing NKT-cell stimulation of CD8 T cells.
4) Ii-targeting with shRNA is effective in reducing NKT-cell stimulation of CD4 T cells.
5) The majority of NKTs remain resistant to allo-NK cell cytotoxicity after CRISPR-mediated B2M knockout and even more so after shRNA-mediated B2M knockdown.
6) Effective expression of CAR and B2M shRNA and/or Ii shRNA in NKTs has been achieved within a single retroviral vector, providing a means for generating CAR-redirected and universally tolerated allogeneic NKT cell products for cancer immunotherapy.

Example 2

Generation of Tumor-Specific and Universally Tolerated Cells Other than NKT Cells from Healthy Donors for Off-the-Shelf Cancer Immunotherapy In certain embodiments, cells other than NKT cells are manipulated to have reduced expression of endogenous B2M and/or Ii. Such cells may be any immune cells other than NKT cells, such as T cells, γ/δ T cells, Mucosal-associated invariant T (MAIT) cells, NK cells, Innate lymphoid cells (ILCs), or mixtures thereof. In some embodiments, a mixture of NKT cells and one or more of immune cells other than NKT cells are utilized in the compositions and methods encompassed by the disclosure.

The non-NKT cells may be manipulated to have reduced expression of endogenous B2M and/or Ii by standard means in the art, such as using one or more agents to target expression of the B2M gene, including nucleic acids such as shRNA or CRISPR guide RNA. Other means include at least morpholinos, siRNA, S-DNA, TALENs, ZFNs and so forth.

In particular embodiments, non-NKT cells used in the compositions and methods of the disclosure are expanded prior to and/or after manipulation of the cells to have reduced expression of endogenous B2M and/or Ii. Routine methods in the art are known for expansion and may include a particular media and one or more particular agents, such as one or more cytokines, for example.

In particular embodiments, one or more types of non-NKT cells for use in compositions or methods of the disclosure may need manipulation other than that needed by a NKT cell to be able to be used effectively. For example, T cells may be modified to prevent damage to a recipient's tissues for rejection. In specific cases, the T cells are manipulated to delete a component of a T cell receptor.

Example 3

Generation of Tumor-Specific and Tolerant NKTs and Other Cells from Healthy Donors for Off-the-Shelf Cancer Immunotherapy by Targeting Mhc Class II-Associated Invariant Chain (Ii)

In some embodiments, alternative to (or in addition to) cells and methods of using same directed to reduced expression of B2M and/or the cells have reduced expression of MHC class II-associated invariant chain (Ii). Such cells may be used in place of cells that have reduced expression of endogenous B2M. In some cases, the same cell has reduced expression of both B2M and Ii, and in some cases a mixture of cells separately having reduced expression of endogenous B2M or reduced expression of endogenous Ii are used. In cases wherein the same cell has reduced expression of endogenous B2M and endogenous Ii, the same type of agent may be used to target their respective reduction in expression. For example, in some cases both B2M and Ii are targeted by shRNA to reduce their expression, or in other cases both B2M and Ii are targeted by CRISPR guide RNA to reduce their expression. In some cases, different agents target B2M and Ii, such as shRNA for targeting B2M and CRISPR guide RNA for targeting Ii, for example.

In particular embodiments, the cells that comprise reduced expression of Ii may also comprise expression of another entity that is non-natural to the cell, such as a cytokine or a CAR, for example. Such additional entities may or may not be expressed from the same construct as the agent that targets expression of Ii. In cases wherein in the same cell both Ii expression is targeted and another entity is provided for expression in the cell, they may be configured in the same construct in any suitable arrangement, such as one being 5' or 3' in relation to the other; they may or may not be regulated by the same regulatory element(s).

The cells may be NKT or may not be NKT cells, such as T cells, γ/δ T cells, MAIT cells, NK cells, ILCs, or mixtures thereof, and T cells may be engineered to lack TCRs.

Example 4

Figure 7:
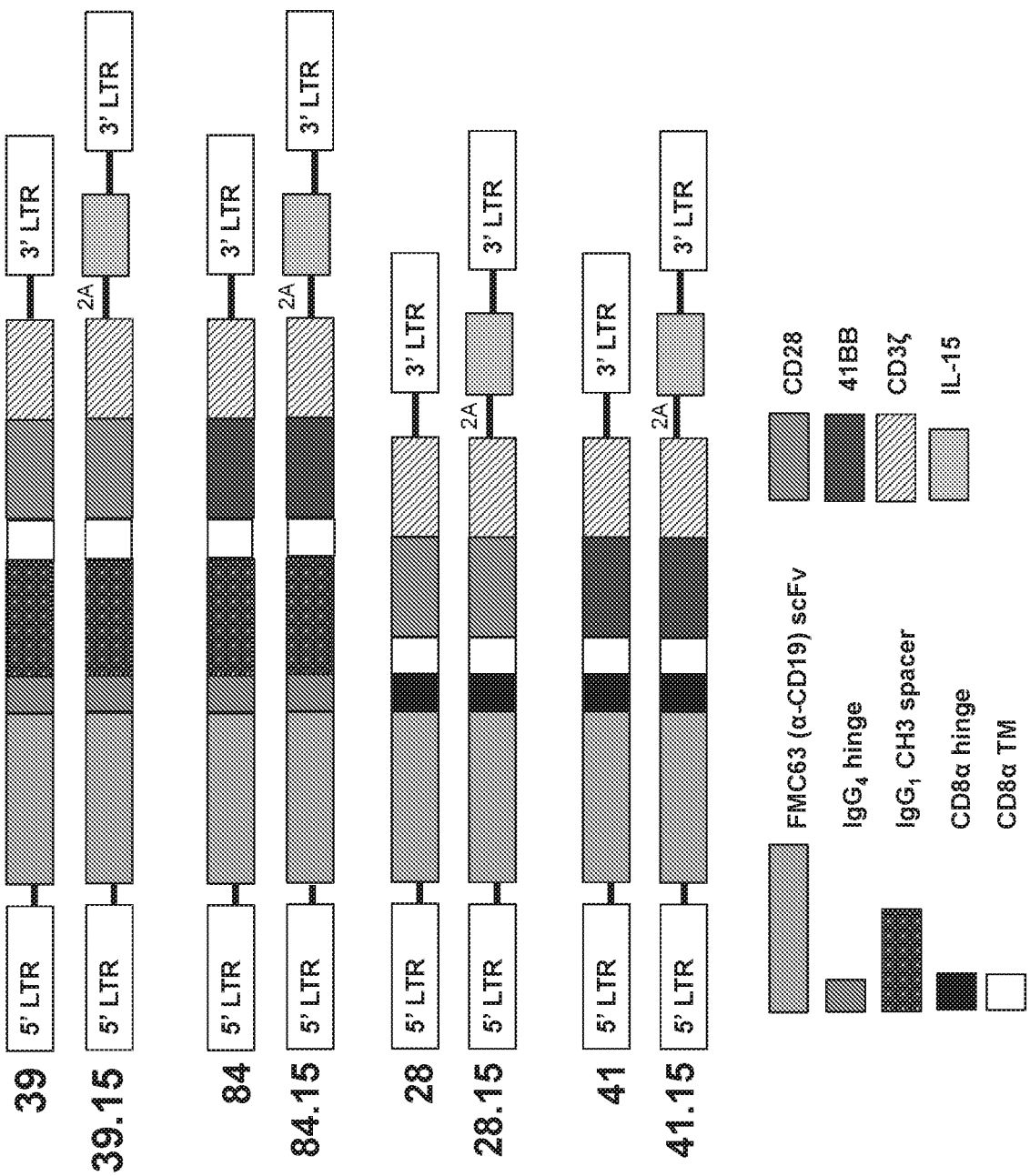
FIG. 7. Generation of CD19 CAR constructs expressing either CD28 or 41BB co-stimulatory domains with or without IL15. Eight constructs were generated based on two domain architectures. The first group (39 and 84 constructs) encode the IgG$_4$ hinge, IgG$_1$ CH3 spacer, CD28 TM, and either a CD28 or 4-1BB co-stimulatory domain, all with or without IL15. The second group (28 and 41 constructs) encode the CD8α hinge and TM with either the CD28 or 4-1BB co-stimulatory domain, all with or without IL15. The 28 and 41 constructs were generated by joining fragments containing either the CD28 or 41BB co-stimulatory domain, respectively, with the FMC63 scFv. The 2A and IL15 sequences were added to all constructs using the Gibson assembly method (New England Biosciences). LTR=long terminal repeat, scFv=single chain variable fragment, TM=transmembrane, 2A=2A sequence from equine rhinitis A virus.

Generation of Tumor-Specific and Tolerant NKTs Expressing Chimeric Antigen Receptors for Off-the-Shelf Cancer Immunotherapy by Targeting Mhc Class II-Associated Invariant Chain (Ii) or B2M CD19 CAR constructs were generated that expressed either CD28 or 41BB co-stimulatory domains with or without IL15 (FIG. 6). The constructs were generated based on two domain architectures: (1) a first group (39 and 84 constructs) that encoded the $IgG_4$ hinge, $IgG_1$ CH3 spacer, CD28 TM, and either a CD28 or 4-1BB co-stimulatory domain, all with or without IL15; and (2) a second group (28 and 41 constructs) that encoded the CD8a hinge and TM with either the CD28 or 4-1BB co-stimulatory domains, all with or without IL15 (FIG. 6A). Alternative or additional co-stimulatory domains may be utilized in such constructs. Respective flow cytometry analysis is shown in FIG. 6B. CD19 CAR construct examples are illustrated in FIG. 7.

Figure 8A:
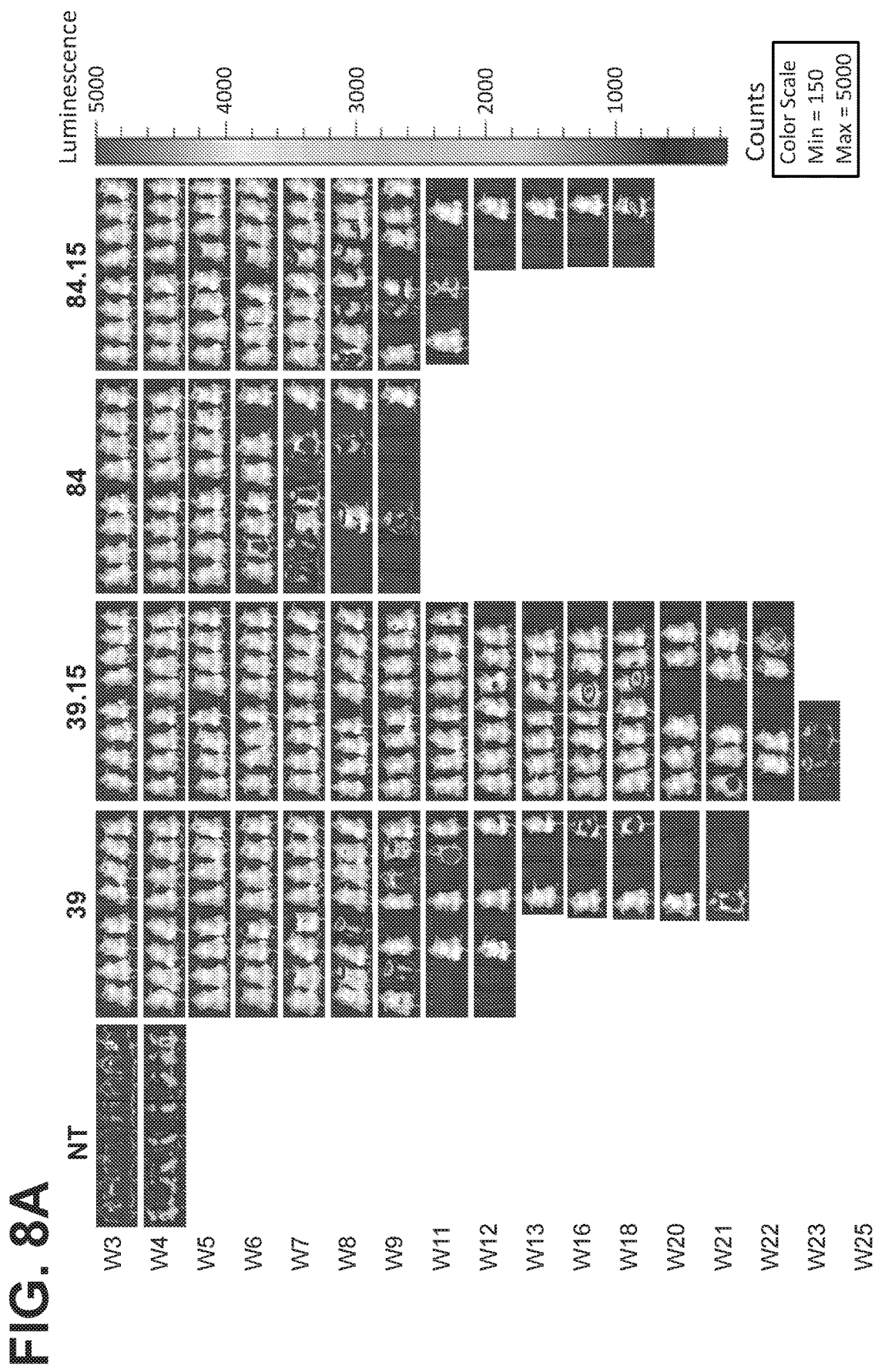
FIG. 8. Serial bioluminescence imaging of firefly luciferase (Ffluc)-labeled Daudi lymphoma cells in mice injected with CD19 CAR NKTs. NSG mice were injected intravenously with 2×10$^5$ Ffluc+ Daudi lymphoma cells followed three days later by intravenous injection of 5×10$^6$ NKTs transduced with indicated constructs or no construct (non-transduced, NT). Just prior to imaging, mice received 100 μL luciferin at 30 mg/mL via intraperitoneal injection and were imaged under a bioluminescent channel for 5 min. Bioluminescent counts scale 150-5000.
Figure 8B:
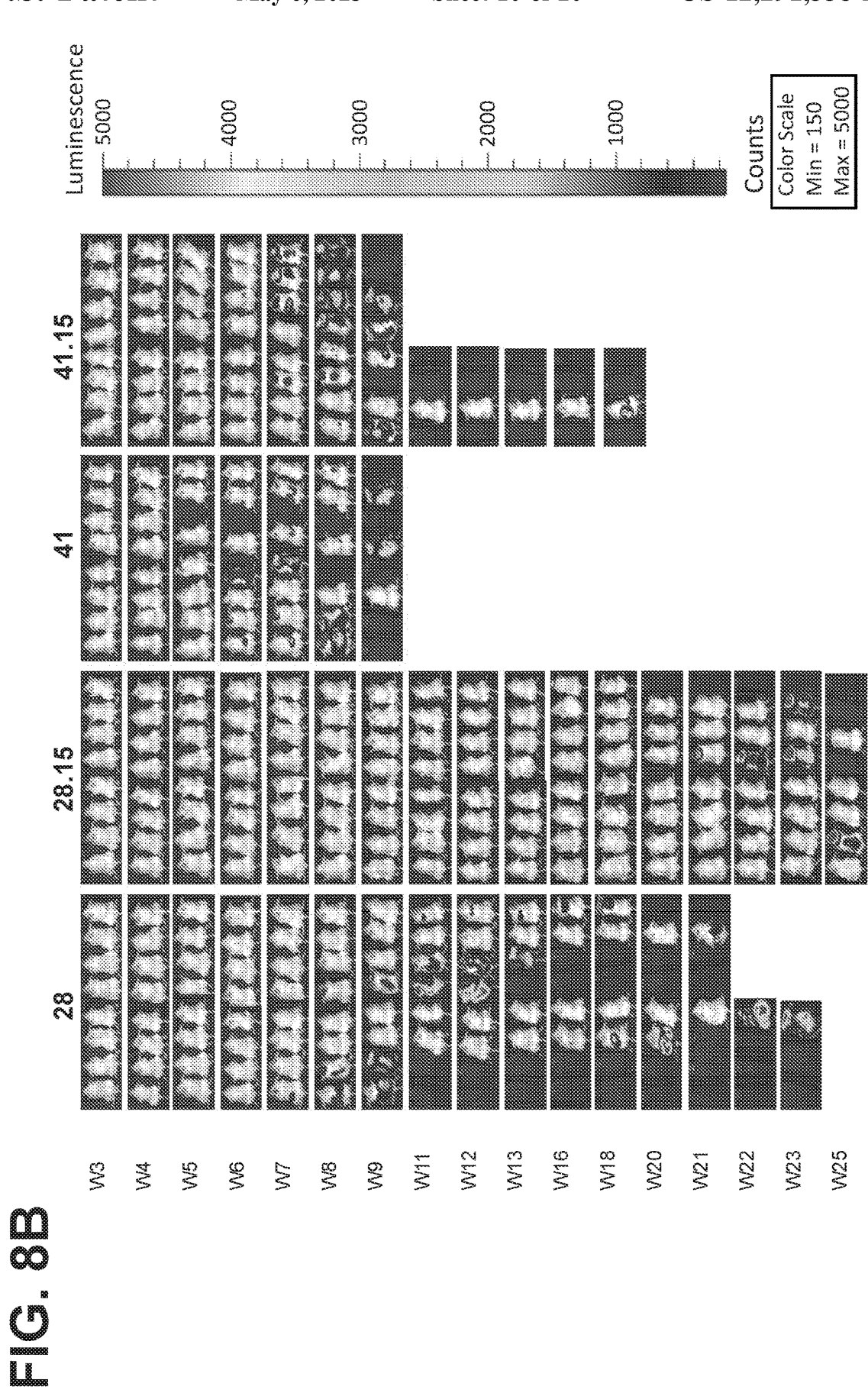
Figure 9:
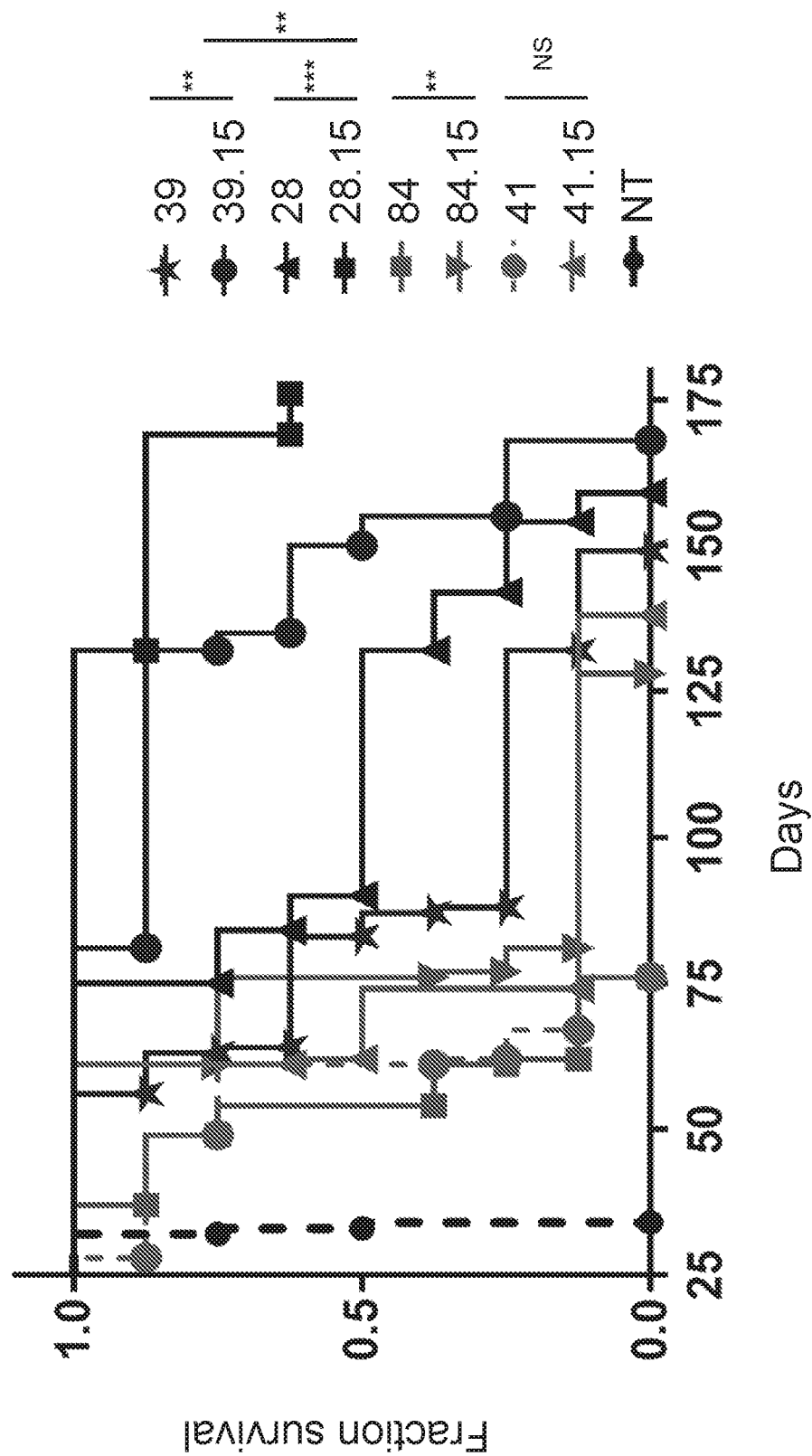
FIG. 9. Survival curves for Daudi lymphoma mice treated with CD19 CAR NKTs in FIG. 8. Survival probability was analyzed by the Kaplan-Meier method (eight mice per group) and comparisons were calculated using the Log-rank (Mantel-Cox) test. 39 vs. 39.15 p=0.0033, 28 vs. 28.15 p=0.0003, 39.15 vs 28.15 p=0.0011, 84 vs. 84.15 p=0.0039, 41 vs. 41.15 p=0.1410.

As shown in FIG. 8, NSG mice were serially imaged that had been injected intravenously with $2 \times 10^5$ Ffluc+Daudi lymphoma cells followed by intravenous injection of $5 \times 10^6$ NKTs transduced with the noted constructs or no construct (non-transduced, NT). Just prior to imaging, the mice received 100 μL luciferin at 30 mg/mL via intraperitoneal injection; they were imaged under a bioluminescent channel for 5 min. Imaging occurred over the course of three to 25 weeks, as an example. FIG. 9 demonstrates survival curves for those mice.

Figure 10:
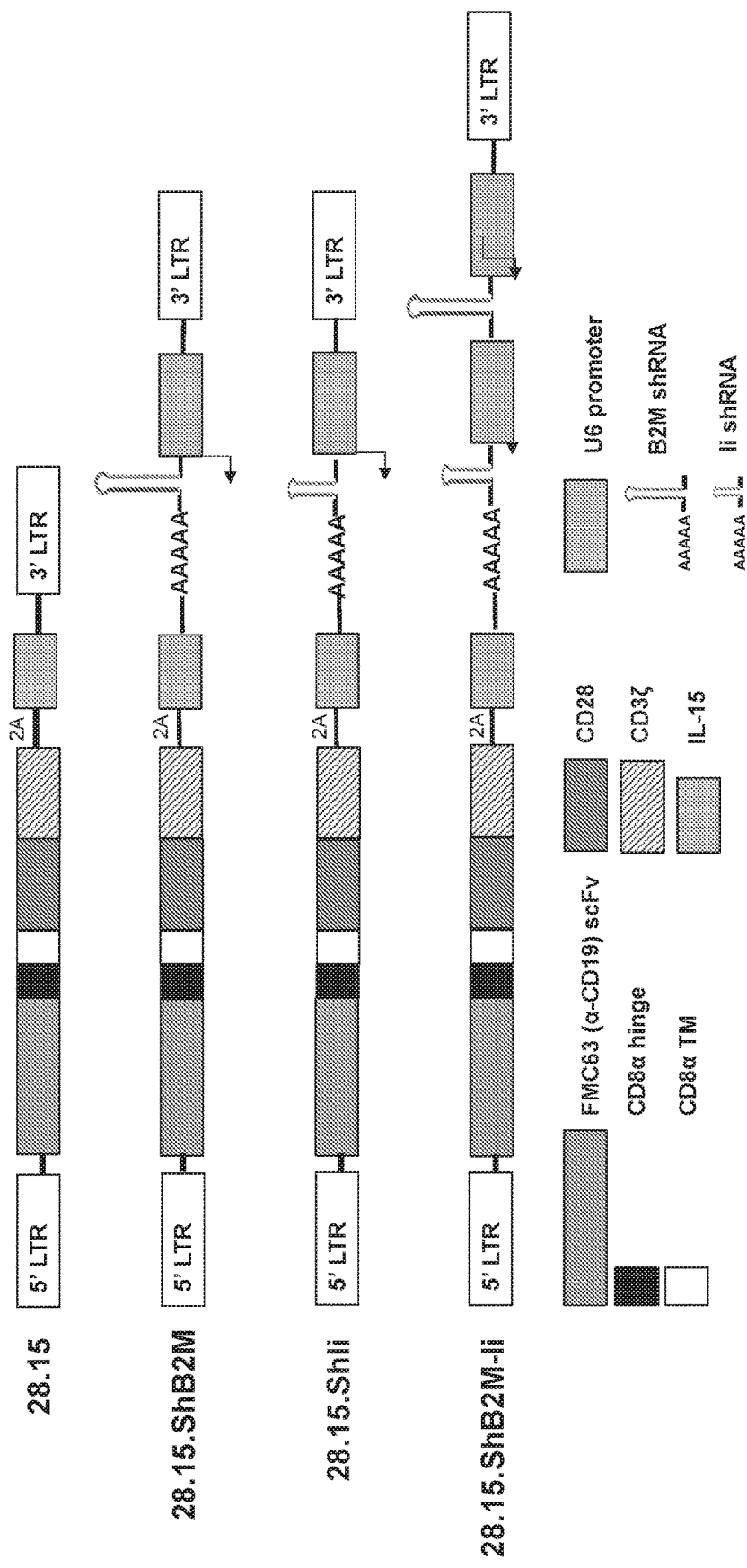
FIG. 10. Generation of retroviral vectors that express CD19 CAR with and without B2M and Ii shRNA. The 28.15 construct was generated as described in FIG. 7. For shRNA-containing constructs, B2M and Ii shRNA sequences linked to individual U6 promoters (Sigma-Aldrich) were ligated individually or together to 28.15 downstream of the CAR in the opposite transcriptional direction by Gibson assembly. LTR=long terminal repeat, scFv=single chain variable fragment, TM=transmembrane, 2A=2A sequence from equine rhinitis A virus.

FIG. 10 illustrates examples of retroviral vectors that express CD19 CAR with and without B2M and Ii shRNA. For those constructs comprising shRNA, B2M and Ii shRNA sequences were linked to individual U6 promoters and were ligated individually or together to 28.15 downstream of the CAR in the opposite transcriptional direction.

FIG. 11 shows shRNA knockdown of B2M and Ii expression with the respective constructs. In FIG. 11A, representative flow cytometry analysis of CD19 CAR expression is provided following transduction of NKTs and staining with Alexa 647-conjugated anti-FMC63 mAb. Representative flow cytometry analyses of (11B) B2M, (11C) HLA ABC, (11D) Ii, and (11E) HLA DP-DQ-DR expression in NKT cells transduced with the indicated constructs are provided. Cells were stained with anti-FMC63 mAb and 1) PE-conjugated anti-B2M antibody with FITC-conjugated anti-HLA ABC antibody or 2) PE-conjugated anti-Ii antibody with FITC-conjugated anti-HLA DP-DQ-DR antibody. FIG. 11F shows quantification of the indicated gene knockdown in CAR-shRNA NKTs versus CAR NKTs.

Figure 12:
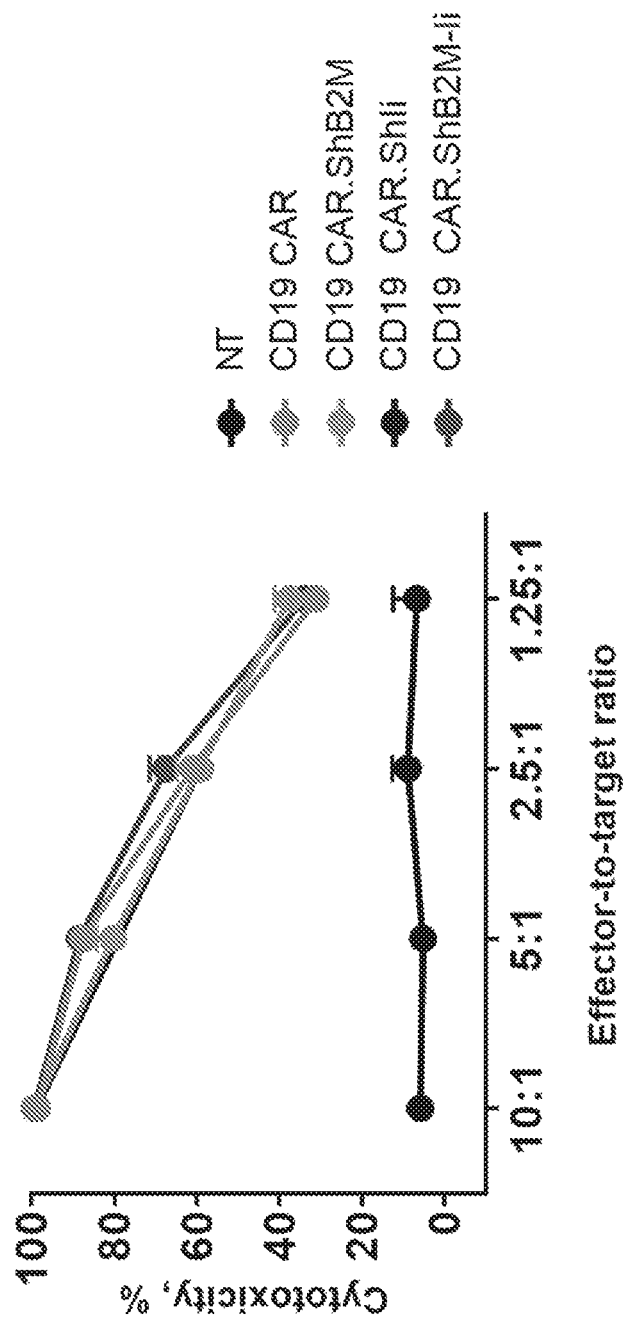
FIG. 12. B2M/Ii shRNAs do not impact CAR-directed in vitro cytotoxicity of CAR $^{UT}$NKT cells. NKTs transduced with the indicated CD19 CAR-shRNA constructs or non-transduced (NT) were co-cultured for six hours with luciferase-positive Daudi (CD19-positive) target cells at the specified effector-to-target ratios. NKT cytotoxicity was determined as a function of target cell bioluminescence following co-culture.

FIG. 12 indicates that the B2M/Ii shRNAs do not impact CAR-directed in vitro cytotoxicity of CAR $^{UT}$NKT cells. NKTs transduced with the indicated CD19 CAR-shRNA constructs or non-transduced (NT) were co-cultured with luciferase-positive Daudi (CD19-positive) target cells at the specified effector-to-target ratios. NKT cytotoxicity was determined as a function of target cell bioluminescence following co-culture.

Figure 13C:
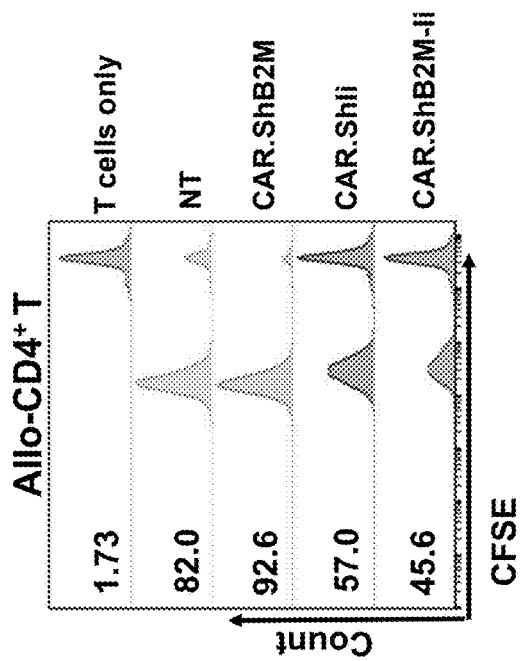
FIGS. 13A, 13B, and 13C. Unmatched CD8$^+$ and CD4$^+$ T cells show diminished alloreactivity to CAR $^{UT}$NKT cells in an allogeneic MLR assay. (13A) Schematic of expected results for T cell in allogeneic MLR assay. Allogeneic CD8$^+$ or CD4$^+$ T cell recognition of MHC class I and MHC class II, respectively, on parental NKTs will lead to T cell proliferation. Downregulation of MHC class I via B2M knockdown or MHC class II via Ii knockdown in $^{UT}$NKTs will lead to a relative decrease in allogeneic T cell proliferation. (13B) CFSE-labeled CD8$^+$ or (13C) CD4$^+$ T cells were co-cultured with CAR $^{UT}$NKT cells expressing indicated constructs or non-transduced (NT) NKT cells at a 1:5 (T:NKT) ratio. T cell proliferation was assessed five days after stimulation as measured by CFSE dilution. Results are from a representative of three donors tested.
Figure 13A:
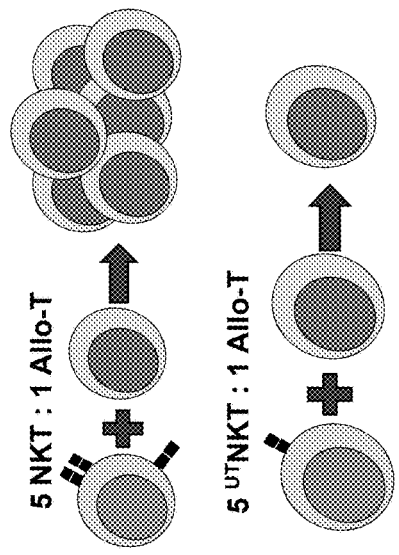
Figure 13B:
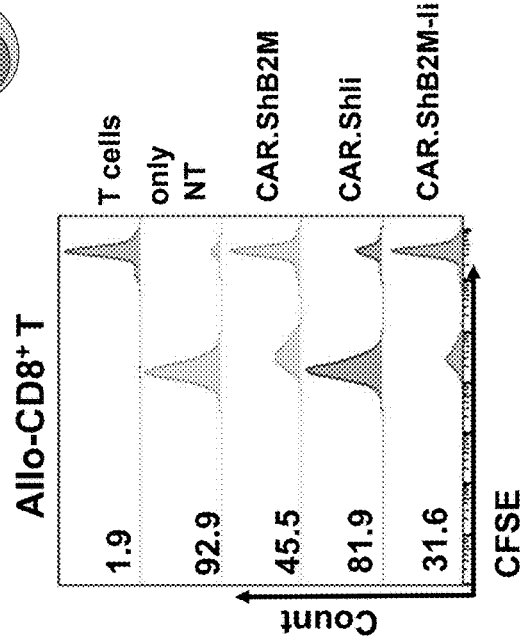

The level of alloreactivity to the CAR $^{UT}$NKT cells was determined in FIG. 13, in which case unmatched $CD8^+$ and $CD4^+$ T cells showed diminished alloreactivity to CAR $^{UT}$NKT cells in an allogeneic mixed lymphocyte reaction (MLR) assay. In FIG. 13A, a schematic of expected results for T cell in allogeneic MLR assay is illustrated. In particular embodiments, allogeneic $CD8^+$ or $CD4^+$ T cell recognition of MHC class I and MHC class II, respectively, on parental NKTs would lead to T cell proliferation. In addition, downregulation of MHC class I via B2M knockdown or MHC class II via Ii knockdown in $^{UT}$NKTs would lead to a relative decrease in allogeneic T cell proliferation. CFSE-labeled $CD8^+$ (FIG. 13B) or $CD4^+$ T cells (FIG. 13C) were co-cultured with CAR $^{UT}$NKT cells expressing the indicated constructs and T cell proliferation was assessed five days after stimulation as measured by CFSE dilution.

The $^{UT}$NKT cells were less susceptible to allogeneic T cell cytotoxicity than parental NKTs. FIG. 14A provides a schematic of predicted results for NKT and $^{UT}$NKT cells in a T cell cytotoxicity assay. Allogeneic T cells would recognize MHC molecules on parental NKTs as foreign, leading to death of these NKT cells. Downregulation of MHC molecules on $^{UT}$NKTs would allow these cells to evade T cell cytotoxicity better than parental NKTs. In FIG. 14B, NKT cell counts were determined by flow cytometry upon incubation of allogeneic T cells with CAR $^{UT}$NKTs or non-transduced (NT) NKTs at a 1:1 ratio for four days.

Figure 15B:
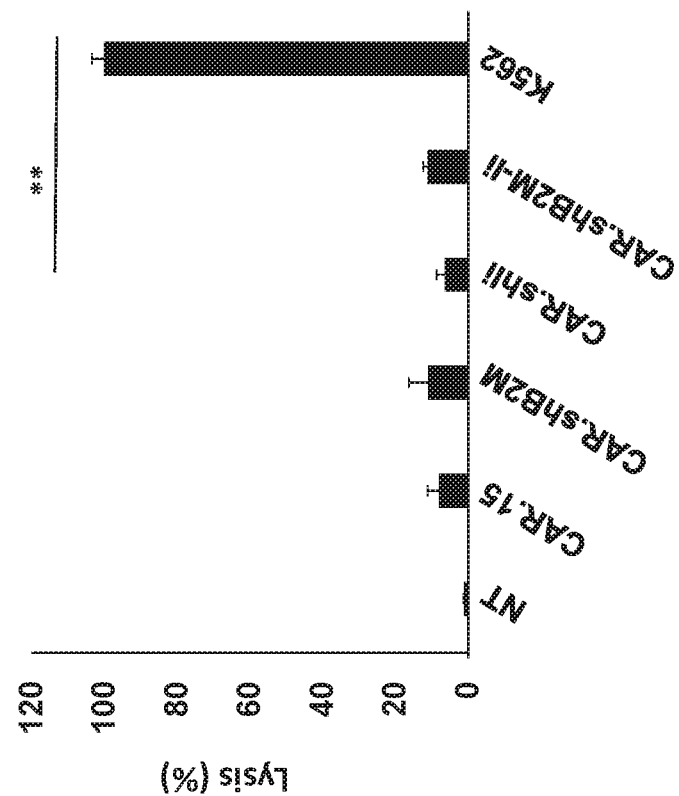
FIGS. 15A and 15B. UTNKT cells are minimally susceptible to NK cell cytotoxicity. (15A) Schematic of expected results for NK cell cytotoxicity assay. NK cells do not kill parental NKTs that express MHC class I, but do usually kill target cells lacking MHC I. $^{UT}$NKTs will express enough MHC I to evade killing by NK cells. (15B) NK cells from healthy donors were co-cultured for four hours with calcein AM-labeled $^{UT}$NKTs at a 5:1 ratio. Target cell lysis is shown as a function of retained calcein-AM fluorescence as determined by flow cytometry, mean±SD, N=3; ** p<0.01. NS: not significant.
Figure 15A:
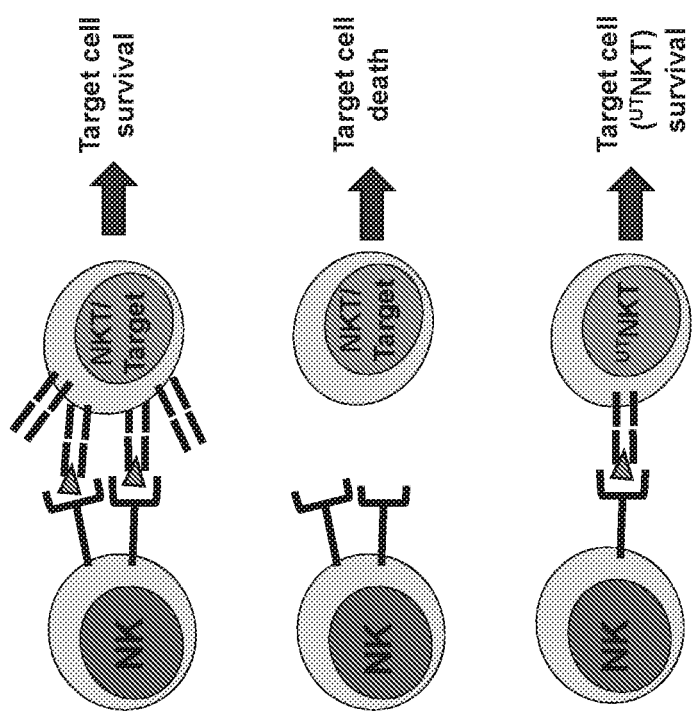

As shown in FIG. 15, $^{UT}$NKT cells are minimally susceptible to NK cell cytotoxicity. FIG. 15A illustrates predicted results for NK cell cytotoxicity assays. As shown, NK cells do not kill parental NKTs that express MHC class I, but do usually kill target cells lacking MHC I. in particular embodiments, $^{UT}$NKTs express enough MHC I to evade killing by NK cells. FIG. 15B demonstrates target cell lysis following co-culture of NK cells from healthy donors with calcein AM-labeled $^{UT}$NKTs at a 5:1 ratio.

Figure 16A:
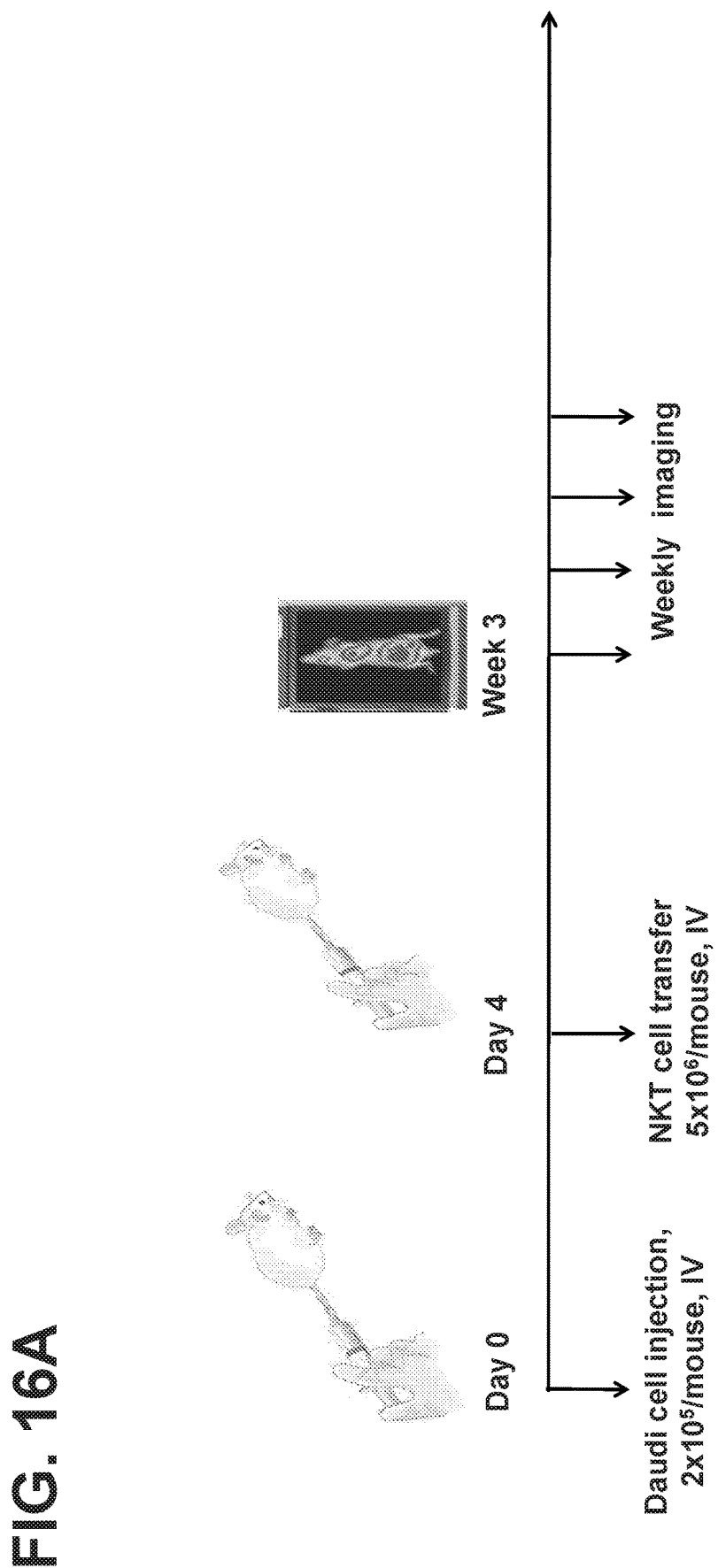
FIGS. 16A and 16B. Serial bioluminescence imaging of Ffluc-labeled Daudi lymphoma cells in mice injected with CAR.CD19 $^{UT}$NKTs. (16A) NSG mice were injected intravenously with 2×10$^5$ Ffluc+Daudi lymphoma cells followed three days later by intravenous injection of 5×10$^6$ CAR.CD19 $^{UT}$NKTs transduced with indicated constructs or no construct (non-transduced, NT). Just prior to imaging, mice received 100 µL luciferin at 30 mg/mL via intraperitoneal injection and were imaged under a bioluminescent channel for 5 min (16B). Bioluminescent counts scale 150-5000.
Figure 16B:
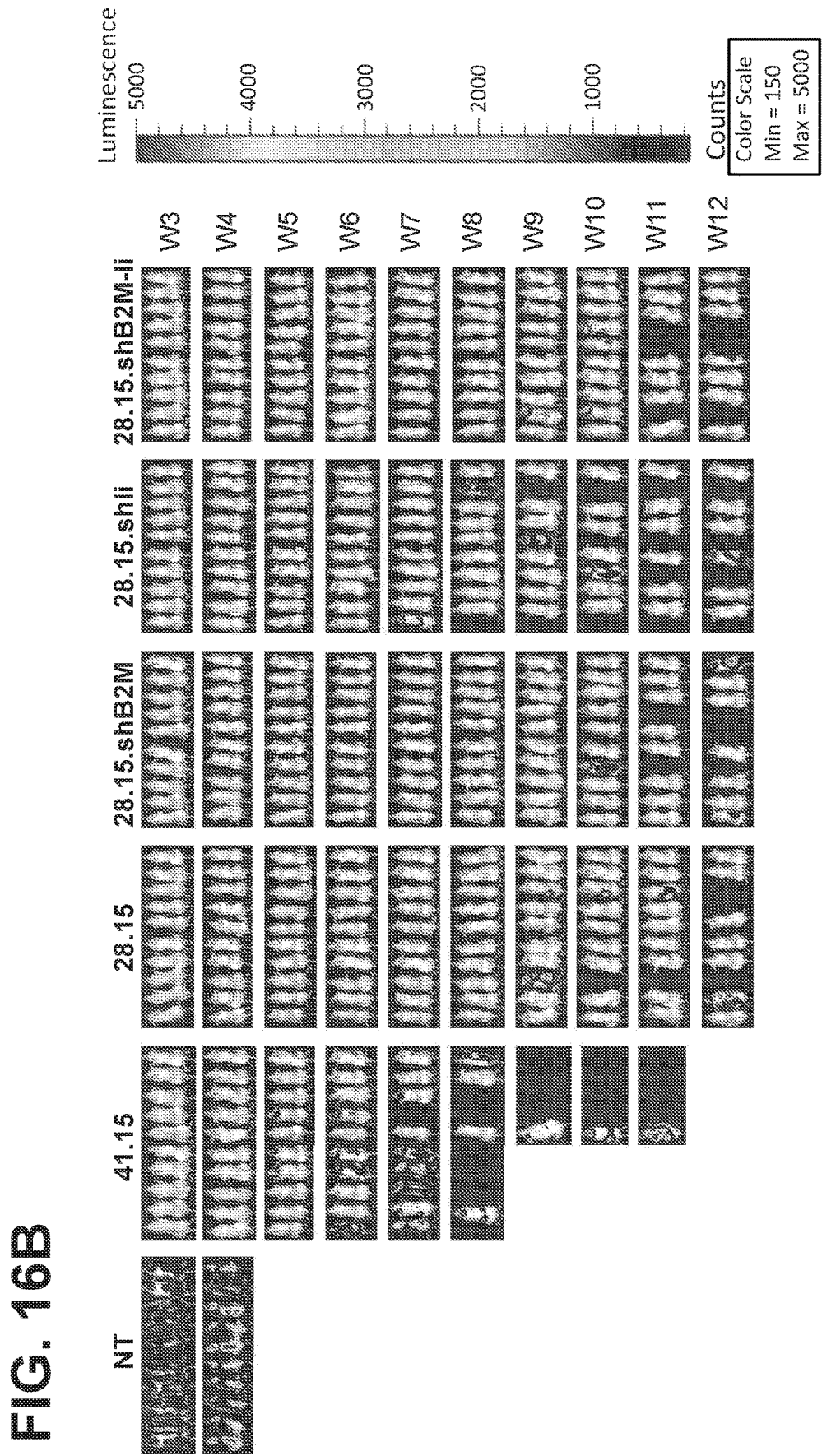
Figure 17:
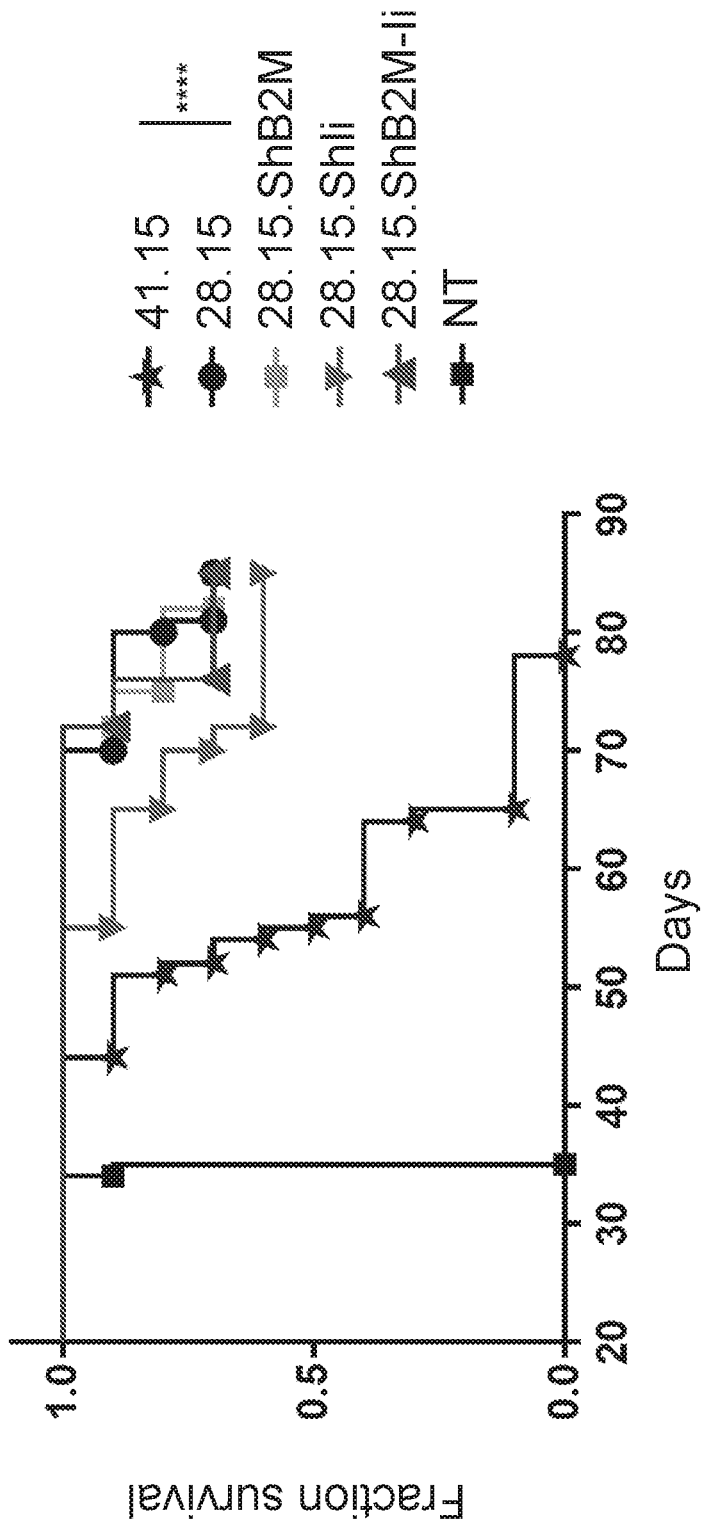
FIG. 17. Survival curves for Daudi lymphoma mice treated with CAR.CD19 $^{UT}$NKTs in FIG. 16. Survival probability was analyzed by the Kaplan-Meier method (10 mice per group) and comparisons were calculated using the Log-rank (Mantel-Cox) test. **** p<0.0001.

Serial bioluminescence imaging of Ffluc-labeled Daudi lymphoma cells in mice injected with CAR.CD19 $^{UT}$NKTs is illustrated in FIG. 16. NSG mice were injected intravenously with $2 \times 10^5$ Ffluc+Daudi lymphoma cells followed by intravenous injection of $5 \times 10^6$ CAR.CD19 $^{UT}$NKTs transduced with indicated constructs or no construct (non-transduced, NT). Corresponding survival curves are provided for the mice in FIG. 17.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.
1. Atkins M B, et al. High-dose recombinant interleukin 2 therapy for patients with metastatic melanoma: analysis of 270 patients treated between 1985 and 1993. *J Clin Oncol* 1999; 17(7):2105-2116.
2. Porter D L, Levine B L, Kalos M, Bagg A, June C H. Chimeric antigen receptor-modified T cells in chronic lymphoid leukemia. *N. Engl. J. Med.* 2011; 365(8):725-733.
3. Grupp S A, et al. Chimeric antigen receptor-modified T cells for acute lymphoid leukemia. *N. Engl. J. Med.* 2013; 368(16):1509-1518.
4. Brentjens R J, et al. CD19-targeted T cells rapidly induce molecular remissions in adults with chemotherapy-refractory acute lymphoblastic leukemia. *Sci. Transl. Med.* 2013; 5(177):177ra138.
5. Kochenderfer J N, et al. B-cell depletion and remissions of malignancy along with cytokine-associated toxicity in a clinical trial of anti-CD19 chimeric-antigen-receptor-transduced T cells. *Blood* 2012; 119(12):2709-2720.
6. Ramos C A, Heslop H E, Brenner M K. CAR-T Cell Therapy for Lymphoma. *Annu. Rev. Med.* 2015.
7. Turtle C J, Maloney D G. Clinical trials of CD19-targeted CAR-modified T cell therapy; a complex and varied landscape. *Expert Rev Hematol* 2016; 9(8):719-721.
8. Singh N, Perazzelli J, Grupp S A, Barrett D M. Early memory phenotypes drive T cell proliferation in patients with pediatric malignancies. *Sci Transl Med* 2016; 8(320): 320ra323.
9. Dudley M E, et al. Cancer regression and autoimmunity in patients after clonal repopulation with antitumor lymphocytes. *Science* 2002; 298(5594):850-854.
10. Tahir S M, et al. Loss of IFN-gamma production by invariant NKT cells in advanced cancer. *J Immunol.* 2001; 167(7):4046-4050.
11. Yanagisawa K, Exley M A, Jiang X, Ohkochi N, Taniguchi M, Seino K. Hyporesponsiveness to natural killer T-cell ligand alpha-galactosylceramide in cancer-bearing state mediated by CD11b+ Gr-1+ cells producing nitric oxide. *Cancer Res.* 2006; 66(23):11441-11446.
12. Dhodapkar M V, et al. A Reversible Defect in Natural Killer T Cell Function Characterizes the Progression of Premalignant to Malignant Multiple Myeloma. *J. Exp. Med.* 2003.
13. Qasim W, et al. Molecular remission of infant B-ALL after infusion of universal TALEN gene-edited CAR T cells. *Sci Transl Med* 2017; 9(374).
14. Porcello S, Yockey C E, Brenner M B, Balk S P. Analysis of T cell antigen receptor (TCR) expression by human peripheral blood CD4-8- alpha/beta T cells demonstrates preferential use of several V beta genes and an invariant TCR alpha chain. *J. Exp. Med.* 1993; 178(1):1-16.
15. Lantz O, Bendelac A. An invariant T cell receptor alpha chain is used by a unique subset of major histocompatibility complex class I-specific CD4+ and CD4-8- T cells in mice and humans. *J. Exp. Med.* 1994; 180(3):1097-1106.
16. Bendelac A, Lantz O, Quimby M E, Yewdell J W, Bennink J R, Brutkiewicz R R. CD1 recognition by mouse NK1+T lymphocytes. *Science* 1995; 268(5212): 863-865.
17. Kim E Y, Lynch L, Brennan P J, Cohen N R, Brenner M B. The transcriptional programs of iNKT cells. *Semin. Immunol.* 2015; 27(1):26-32.
18. Metelitsa L S. Anti-tumor potential of type-I NKT cells against CD1d-positive and CD1d-negative tumors in humans. *Clin. Immunol.* 2011; 140(2):119-129.
19. Heczey A, et al. Invariant NKT cells with chimeric antigen receptor provide a novel platform for safe and effective cancer immunotherapy. *Blood* 2014; 124(18): 2824-2833.
20. Tian G, et al. CD62L+ NKT cells have prolonged persistence and antitumor activity in vivo. *J Clin Invest* 2016; 126(6):2341-2355.
21. Pillai A B, George T I, Dutt S, Teo P, Strober S. Host NKT cells can prevent graft-versus-host disease and permit graft antitumor activity after bone marrow transplantation. *J. Immunol.* 2007; 178(10):6242-6251.
22. Morris E S, et al. NKT cell-dependent leukemia eradication following stem cell mobilization with potent G-CSF analogs. *J. Clin. Invest* 2005; 115(11):3093-3103.
23. Krangel M S, Orr H T, Strominger J L. Assembly and maturation of HLA-A and HLA-B antigens in vivo. *Cell* 1979; 18(4):979-991.
24. Lanier L L. NK cell recognition. *Annu Rev Immunol* 2005; 23:225-274.
25. Gundry M C, et al. Highly Efficient Genome Editing of Murine and Human Hematopoietic Progenitor Cells by CRISPR/Cas9. *Cell Rep* 2016; 17(5):1453-1461.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A modified isolated CD1d-restricted human natural killer T (NKT) cell or a plurality of cells thereof, having, when compared to an unmodified CD1d-restricted human NKT cell, reduced but detectable expression of:
   (a) endogenous beta-2-microglobulin (B2M) and
   (b) endogenous MHC class II-associated invariant chain (Ii); and
   wherein the modified cell or cells comprise synthetic DNA or RNA that targets a gene encoding B2M or a gene encoding Ii.

2. The modified cell or cells of claim 1, wherein the synthetic DNA or RNA targets the 3' end of the B2M gene or Ii gene.

3. The modified cell or cells of claim 1, wherein the synthetic RNA is a shRNA.

4. The modified cell or cells of claim 1, wherein the modified cell or cells comprises one or more recombinantly engineered receptors.

5. The modified cell or cells of claim 4, wherein the one or more receptors is a chimeric antigen receptor, chimeric cytokine receptor, a T cell receptor, or a combination thereof.

6. The modified cell or cells of claim 1 wherein the modified cell or cells recombinantly expresses one or more cytokines.

7. The modified cell or cells of claim 6, wherein the one or more cytokines is IL-15, IL-7, IL-12, IL-18, IL-21, IL-27, IL-33, or a combination thereof.

8. The modified cell or cells of claim 1, further having reduced expression of another endogenous gene besides B2M and Ii.

9. The modified cell or cells of claim 1, wherein the modified cell or cells are NKT cells that are CD62L-positive and/or CD4-positive and/or PD 1-negative/low cells.

10. The modified cell or cells of claim 1, wherein the modified cell or cells are autologous in reference to a subject.

11. The modified cell or cells of claim 1, wherein the modified cell or cells are allogeneic in reference to a subject.

12. A method of generating the modified cell or cells of claim 1, the method comprising exposing the unmodified CD1d-restricted NKT cells to:
   one or more agents that reduce expression of endogenous B2M in the cell or cells and one or more agents that reduce expression of endogenous Ii in the cell or cells, thereby generating the modified cell or cells.

13. The method of claim 12, wherein each of the one or more agents is a DNA vector, morpholinos, siRNA, SDNA, shRNA, or a combination thereof.

14. The method of claim 12, wherein the modified NKT cell or cells are additionally manipulated to express a recombinantly engineered receptor and/or one or more cytokines.

15. A method of treating one or more medical conditions in a subject in need thereof, comprising the step of providing a therapeutically amount of the modified cell or cells of claim 1 to the subject.

16. The method of claim 15, wherein the medical condition is cancer or a premalignant condition.

17. The method of claim 16, wherein the cancer is neuroblastoma, breast cancer, cervical cancer, ovary cancer, endometrial cancer, melanoma, bladder cancer, lung cancer, pancreatic cancer, colon cancer, prostate cancer, hematopoietic tumors of lymphoid lineage, leukemia, acute lymphocytic leukemia, chronic lymphocytic leukemia, B-cell lymphoma, Burkitt's lymphoma, multiple myeloma, Hodgkin's lymphoma, Non-Hodgkin's lymphoma, myeloid leukemia, acute myelogenous leukemia (AML), chronic myelogenous leukemia, thyroid cancer, thyroid follicular cancer, tumors of mesenchymal origin, fibrosarcoma, rhabdomyosarcomas, melanoma, uveal melanoma, teratocarcinoma, neuroblastoma, glioma, glioblastoma, benign tumor of the skin, renal cancer, anaplastic large-cell lymphoma, esophageal squamous cells carcinoma, hepatocellular carcinoma, follicular dendritic cell carcinoma, intestinal cancer, muscle-invasive cancer, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, prostatic hypertrophy, myelodysplasia, Waldenstrom's macroglobinaemia, nasopharyngeal, neuroendocrine cancer myelodysplastic syndrome, mesothelioma, angiosarcoma, Kaposi's sarcoma, carcinoid, oesophagogastric, fallopian tube cancer, peritoneal cancer, papillary serous mullerian cancer, malignant ascites, gastrointestinal stromal tumor (GIST), or a hereditary cancer syndrome selected from Li-Fraumeni syndrome and Von Hippel-Lindau syndrome (VHL), or wherein the premalignant condition is myelodysplastic syndrome (MDS).

18. The method of claim 16, wherein the subject has cancer and is provided an additional cancer therapy.

19. The method of claim 18, wherein the additional cancer therapy is surgery, radiation, chemotherapy, immunotherapy, proton therapy, hormone therapy, or a combination thereof.

20. The method of claim 1, wherein the endogenous beta-2-microglobulin (B2M) has a reduced expression of between 60-90% in the modified cell or cells compared to the unmodified cell and wherein the endogenous MHC class II-associated invariant chain (Ii) has a reduced expression of between 51.2% and 75.6% in the modified cell or cells compared to the unmodified cell.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ggccacggag cgagacatct                                            20

<210> SEQ ID NO 2
<211> LENGTH: 62
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 2
gtaccggagg tttgaagatg ccgcatttct cgagaaatgc ggcatcttca aacctttttt    60
tg                                                                   62

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccggctggtc tttctatctc ttgtactcga gtacaagaga tagaaagacc agttttg      58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccggcagcag agaatggaaa gtcaactcga gttgactttc cattctctgc tgttttg      58

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cggtccgaca ttgaagttga cttactcgag taagtcaact tcaatgtcgg atttttg       57

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggcccaag atagttaagt gggatctcga gatcccactt aactatcttg ggttttg      58

<210> SEQ ID NO 7
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ccgggaccat agactggaag gtcttctcga gaagaccttc cagtctatgg tctttt        57

<210> SEQ ID NO 8
<211> LENGTH: 57
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 8
ccggccacca agtatggcaa catgactcga gtcatgttgc catacttggt ggttttt        57

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ccggcgcgac cttatctcca acaatctcga gattgttgga gataaggtcg cgttttt        57

<210> SEQ ID NO 10
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccggccacac agctacagct ttcttctcga gaagaaagct gtagctgtgt ggttttt        57

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccgggagaac ctgagacacc ttaagctcga gcttaaggtg tctcaggttc tcttttttg      59

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctggtctttc tatctcttgt actcgagtac aagagataga aagaccag                  48

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaccatagac tggaaggtct tctcgagaag accttccagt ctatggtc                  48
```